United States Patent
Lavi et al.

(10) Patent No.: US 10,395,774 B2
(45) Date of Patent: Aug. 27, 2019

(54) VASCULAR FLOW ASSESSMENT

(71) Applicant: CathWorks Ltd, Kfar Saba (IL)

(72) Inventors: Ifat Lavi, Moshav Mishmeret (IL); Ran Kornowski, Ramat-HaSharon (IL); Idit Avrahami, Rosh HaAyin (IL); Nessi Benishti, Kfar-Saba (IL); Guy Lavi, Moshav Mishmeret (IL)

(73) Assignee: Cathworks Ltd, Kfar Saba (IL)

( * ) Notice: Subject to any disclaimer, the term of this patent is extended or adjusted under 35 U.S.C. 154(b) by 0 days.

(21) Appl. No.: 16/200,230

(22) Filed: Nov. 26, 2018

(65) Prior Publication Data

US 2019/0164649 A1    May 30, 2019

Related U.S. Application Data

(63) Continuation of application No. 15/985,359, filed on May 21, 2018, now Pat. No. 10,141,074, which is a
(Continued)

(51) Int. Cl.
*G16H 50/30* (2018.01)
*G16H 30/20* (2018.01)
(Continued)

(52) U.S. Cl.
CPC ............ *G16H 50/30* (2018.01); *A61B 5/026* (2013.01); *A61B 5/02007* (2013.01); *A61B 5/1075* (2013.01); *A61B 6/504* (2013.01); *A61B 6/5235* (2013.01); *G06T 7/00* (2013.01); *G06T 7/0012* (2013.01); *G06T 17/00* (2013.01); *G16H 30/20* (2018.01); *G16H 50/50* (2018.01); *A61B 5/021* (2013.01); *A61B 5/7289* (2013.01);
(Continued)

(58) Field of Classification Search
CPC ....................................................... G16H 50/30
See application file for complete search history.

(56) References Cited

U.S. PATENT DOCUMENTS

| | | | |
|---|---|---|---|
| 6,949,080 B2 * | 9/2005 | Wolf | A61B 5/0031 424/426 |
| 8,155,411 B2 * | 4/2012 | Hof | G06T 7/0012 382/128 |

(Continued)

*Primary Examiner* — Anand P Bhatnagar
(74) *Attorney, Agent, or Firm* — K&L Gates LLP

(57) ABSTRACT

A vascular assessment apparatus is disclosed. The apparatus is configured to receive medical images of a coronary vessel tree of a subject from a medical imaging device and analyze the medical images to identify vessel segments within the coronary vessel tree. For each identified vessel segment, the apparatus is configured to analyze portions of the segment to determine at least one of a radius, diameter, or cross-sectional area of the vessel segment at the analyzed portions, determine resistances for the analyzed portions of the vessel segment based the radius, diameter, or the cross-sectional area at the analyzed portions, and combine the determined resistances for the analyzed portions of the vessel segment to determine a total resistance of the identified vessel segment. The example apparatus is also configured to determine flow rates at each identified vessel segment and calculate an index indicative of vascular function based on the determined flow rates.

24 Claims, 10 Drawing Sheets

Related U.S. Application Data continuation of application No. 15/640,138, filed on Jun. 30, 2017, now Pat. No. 9,977,869, which is a continuation of application No. 14/040,688, filed on Sep. 29, 2013, now Pat. No. 9,858,387.

(60) Provisional application No. 61/752,526, filed on Jan. 15, 2013.

(51) Int. Cl.

| | | |
|---|---|---|
| *A61B 5/107* | (2006.01) | |
| *A61B 5/026* | (2006.01) | |
| *A61B 5/02* | (2006.01) | |
| *G06T 7/00* | (2017.01) | |
| *A61B 6/00* | (2006.01) | |
| *G06T 17/00* | (2006.01) | |
| *G16H 50/50* | (2018.01) | |
| *A61B 6/03* | (2006.01) | |
| *A61B 8/06* | (2006.01) | |
| *A61B 5/021* | (2006.01) | |
| *A61B 5/00* | (2006.01) | |

(52) U.S. Cl.
CPC ............... *A61B 6/032* (2013.01); *A61B 6/037* (2013.01); *A61B 6/481* (2013.01); *A61B 6/507* (2013.01); *A61B 6/5217* (2013.01); *A61B 6/541* (2013.01); *A61B 8/06* (2013.01); *A61B 2576/023* (2013.01); *G06T 2200/04* (2013.01); *G06T 2207/10072* (2013.01); *G06T 2207/10116* (2013.01); *G06T 2207/10132* (2013.01); *G06T 2207/30101* (2013.01); *G06T 2207/30104* (2013.01); *G06T 2207/30172* (2013.01)

(56) References Cited

U.S. PATENT DOCUMENTS

| | | | | |
|---|---|---|---|---|
| 8,157,742 B2* | 4/2012 | Taylor | ............... | A61B 5/02007 600/504 |
| 9,314,584 B1* | 4/2016 | Riley | ............... | A61M 25/00 |
| 9,615,755 B2* | 4/2017 | Riley | ............... | A61M 25/00 |
| 10,034,614 B2* | 7/2018 | Edic | ............... | G06T 7/30 |
| 10,217,220 B2* | 2/2019 | Kassab | ............... | A61B 6/507 |
| 2002/0165479 A1* | 11/2002 | Wilk | ............... | A61B 5/0031 604/8 |
| 2003/0097172 A1* | 5/2003 | Shalev | ............... | A61F 2/88 623/1.31 |
| 2003/0204160 A1* | 10/2003 | Kamm | ............... | G16H 50/50 604/8 |
| 2010/0021025 A1* | 1/2010 | Hof | ............... | G06T 7/0012 382/128 |
| 2010/0121204 A1* | 5/2010 | Utsuno | ............... | A61B 5/02007 600/485 |
| 2010/0298719 A1* | 11/2010 | Kock | ............... | A61B 5/02028 600/485 |
| 2011/0015530 A1* | 1/2011 | Misawa | ............... | G09B 23/30 600/481 |
| 2011/0071404 A1* | 3/2011 | Schmitt | ............... | A61B 5/0066 600/479 |
| 2012/0041324 A1* | 2/2012 | Taylor | ............... | A61B 5/02007 600/508 |
| 2012/0150516 A1* | 6/2012 | Taylor | ............... | A61B 5/02007 703/9 |
| 2013/0132054 A1* | 5/2013 | Sharma | ............... | G16B 5/00 703/9 |
| 2013/0226003 A1* | 8/2013 | Edic | ............... | G06T 7/30 600/454 |
| 2013/0243294 A1* | 9/2013 | Ralovich | ............... | G06T 7/0012 382/131 |
| 2013/0246034 A1* | 9/2013 | Sharma | ............... | A61B 5/02007 703/11 |
| 2014/0107935 A1* | 4/2014 | Taylor | ............... | A61B 5/02007 702/19 |
| 2016/0110866 A1* | 4/2016 | Taylor | ............... | A61B 5/02007 382/131 |
| 2016/0220126 A1* | 8/2016 | Riley | ............... | A61M 25/00 |
| 2016/0350920 A1* | 12/2016 | Kassab | ............... | A61B 6/507 |
| 2017/0076043 A1* | 3/2017 | Dormer | ............... | G06F 21/6254 |
| 2017/0281018 A1* | 10/2017 | Kramer | ............... | G16H 50/50 |
| 2018/0089829 A1* | 3/2018 | Zhong | ............... | A61B 6/032 |

\* cited by examiner

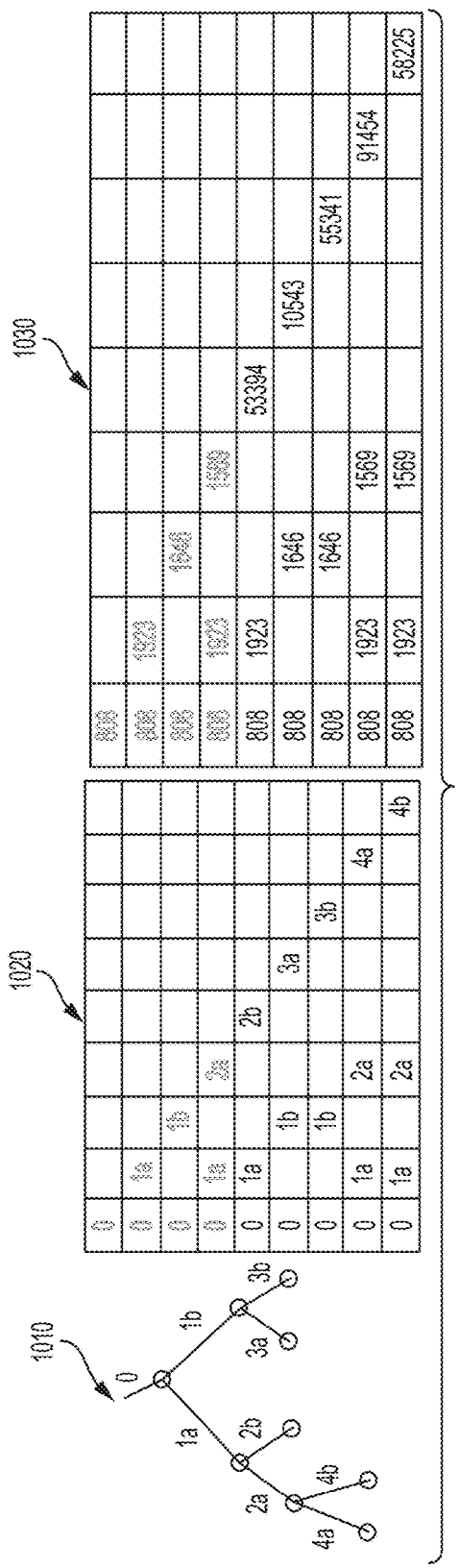
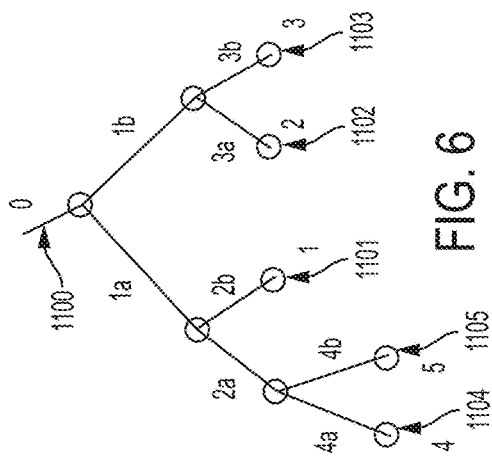
FIG. 5
FIG. 6

VASCULAR FLOW ASSESSMENT

PRIORITY CLAIM

The present application is a continuation of, claims priority to and the benefit of U.S. patent application Ser. No. 15/985,359, now U.S. Pat. No. 10,141,074 filed on May 21, 2018, which is a continuation of, claims priority to and the benefit of U.S. patent application Ser. No. 15/640,138, now U.S. Pat. No. 9,977,869, filed on Jun. 30, 2017, which is a continuation of, claims priority to and the benefit of U.S. patent application Ser. No. 14/040,688, now U.S. Pat. No. 9,858,387, filed on Sep. 29, 2013, which claims priority to and the benefit of U.S. Provisional Patent Application No. 61/752,526, filed on Jan. 15, 2013, the entirety of which are incorporated herein by reference.

FIELD

The present invention, in some embodiments thereof, relates to vascular flow assessment and, more particularly, but not exclusively, to modeling vascular flow and to assessing vascular flow.

BACKGROUND

Arterial stenosis is one of the most serious forms of arterial disease. In clinical practice, stenosis severity is estimated by using either simple geometrical parameters, such as determining the percent diameter of a stenosis, or by measuring hemodynamically based parameters, such as the pressure-based myocardial Fractional Flow Reserve (FFR). FFR is an invasive measurement of the functional significance of coronary stenoses. The FFR measurement technique involves insertion of a 0.014" guidewire equipped with a miniature pressure transducer located across the arterial stenosis. It represents the ratio between the maximal blood flow in the area of stenosis and the maximal blood flow in the same territory without stenosis. Earlier studies showed that FFR<0.75 is an accurate predictor of ischemia and deferral of percutaneous coronary intervention for lesions with FFR≥0.75 appeared to be safe.

An FFR cut-off value of 0.8 is typically used in clinical practice to guide revascularization, supported by long-term outcome data. Typically, an FFR value in a range of 0.75-0.8 is considered a 'grey zone' having uncertain clinical significance.

Modeling vascular flow and assessing vascular flow is described, for example, in U.S. published patent application number 2012/0059246 of Taylor, to a "Method And System For Patient-Specific Modeling Of Blood Flow", which describes embodiments which include a system for determining cardiovascular information for a patient. The system may include at least one computer system configured to receive patient-specific data regarding a geometry of at least a portion of an anatomical structure of the patient. The portion of the anatomical structure may include at least a portion of the patient's aorta and at least a portion of a plurality of coronary arteries emanating from the portion of the aorta. The at least one computer system may also be configured to create a three-dimensional model representing the portion of the anatomical structure based on the patient-specific data, create a physics-based model relating to a blood flow characteristic within the portion of the anatomical structure, and determine a fractional flow reserve within the portion of the anatomical structure based on the three-dimensional model and the physics-based model.

Additional background art includes:

U.S. Published Patent Application No. 2012/053918 of Taylor;

U.S. Published Patent Application No. 2012/0072190 of Sharma et al;

U.S. Published Patent Application No. 2012/0053921 of Taylor;

U.S. Published Patent Application No. 2010/0220917 of Steinberg et al;

U.S. Published Patent Application No. 2010/0160764 of Steinberg et al;

U.S. Published Patent Application No. 2012/0072190 of Sharma et al;

U.S. Pat. No. 6,236,878 to Taylor et al;

U.S. Pat. No. 8,311,750 to Taylor;

an article titled: "Determination of fractional flow reserve (FFR) based on scaling laws: a simulation study" by Jerry T. Wong and Sabee Molloi, published in Phys. Med. Biol. 53 (2008) 3995-4011;

an article titled: "A Scheme for Coherence-Enhancing Diffusion Filtering with Optimized Rotation Invariance", by Weickert, published in Journal of Visual Communication and Image Representation; Volume 13, Issues 1-2, March 2002, Pages 103-118 (2002);

a thesis in a book titled "Anisotropic Diffusion in Image Processing", by J. Weickert, published by B. G. Teubner (Stuttgart) in 1998;

an article titled: "Multiscale vessel enhancement filtering", by A. F Frangi, W. J. Niessen, K. L. Vincken, M. A. Viergever, published in Medical Image Computing and Computer-Assisted Intervention—MICCA '98;

an article titled: "Determination of fractional flow reserve (FFR) based on scaling laws: a simulation study", by Jerry T Wong and Sabee Molloi, published in Phys. Med. Biol. 53 (2008) 3995-4011;

an article titled: "Quantification of Fractional Flow Reserve Using Angiographic Image Data", by S. Molloi, J. T. Wong, D. A. Chalyan, and H. Le, published in O. Dössel and W. C. Schlegel (Eds.): WC 2009, IFMBE Proceedings 25/II, pp. 901-904, 2009;

an article titled: "Quantification of fractional flow reserve based on angiographic image data", by Jerry T. Wong, Huy Le, William M. Suh, David A. Chalyan, Toufan Mehraien, Morton J. Kern, Ghassan S. Kassab, and Sabee Molloi, published in Int J Cardiovasc Imaging (2012) 28:13-22;

an article titled: "An angiographic technique for coronary fractional flow reserve measurement: in vivo validation", by Shigeho Takarada, Zhang Zhang and Sabee Molloi, published online on 31 Aug. 2012 in Int J Cardiovasc Imaging;

an article titled: "A new algorithm for deriving pulsatile blood flow waveforms tested using stimulated dynamic angiographic data", by A. M. Seifalian, D. J. Hawkes, A. C. Colchester, and K. E. Hobbs, published in Neuroradiology, vol. 31, no. 3, pp. 263269, 1989;

an article titled: "Validation of a quantitative radiographic technique to estimate pulsatile blood flow waveforms using digital subtraction angiographic data", by A. M. Seifalian, D. J. Hawkes, C. R. Hardingham, A. C. Colchester, and J. F. Reidy, published in J. Biomed. Eng., vol. 13, no. 3 pp. 225233, May 1991;

an article titled: "Validation of volume blood flow measurements using three dimensional distance-concentration functions derived from digital X-ray angiograms", by D. J. Hawkes, A. M. Seifalian, A. C. Colchester, N. Iqbal, C.

R. Hardingham, C. F. Bladin, and K. E. Hobbs, published in Invest. Radiol, vol. 29, no. 4, pp. 434442, April 1994;

an article titled: "Blood flow measurements using 3D distance-concentration functions derived from digital X-ray angiograms", by A. M. Seifalian, D. J. Hawkes, C. Bladin, A. C. F. Colchester, and K. E. F. Hobbs, published in Cardiovascular Imaging, J. H. C. Reiber and E. E. van der Wall, Eds. Norwell, Mass., The Netherlands: Kluwer Academic, 1996, pp. 425-442;

an article titled: "Determination of instantaneous and average blood flow rates from digital angiograms of vessel phantoms using distance-density curves", by K. R. Hoffmann, K. Doi, and L. E. Fencil, published in Invest. Radiol, vol. 26, no. 3, pp. 207212, March 1991;

an article titled: "Comparison of methods for instantaneous angiographic blood flow measurement", by S. D. Shpilfoygel, R. Jahan, R. A. Close, G. R. Duckwiler, and D. J. Valentino, published in Med. Phys., vol. 26, no. 6, pp. 862871, June 1999;

an article titled: "Quantitative angiographic blood flow measurement using pulsed intra-arterial injection", by D. W. Holdsworth, M. Drangova, and A. Fenster, published in Med. Phys., vol. 26, no. 10, pp. 21682175, October 1999;

an article titled: "Dedicated bifurcation analysis: basic principles", by Joan C. Tuinenburg, Gerhard Koning, Andrei Rares, Johannes P. Janssen, Alexandra J. Lansky, Johan H. C. Reiber, published in Int J Cardiovasc Imaging (2011) 27:167174;

an article titled: "Quantitative Coronary Angiography in the Interventional Cardiology", by Salvatore Davide Tomasello, Luca Costanzo and Alfredo Ruggero Galassi, published in Advances in the Diagnosis of Coronary Atherosclerosis;

an article titled: "New approaches for the assessment of vessel sizes in quantitative (cardio-)vascular X-ray analysis", by Johannes P. Janssen, Andrei Rares, Joan C. Tuinenburg, Gerhard Koning, Alexandra J. Lansky, Johan H. C. Reiber, published in Int J Cardiovasc Imaging (2010) 26:259271;

an article titled: "Coronary obstructions, morphology and physiologic significance Quantitative Coronary Arteriography" by Kirkeeide R L. ed. Reiber J H C and Serruys P W, published by The Netherlands: Kluwer, 1991, pp 229-44;

an article titled: "Coronary x-ray angiographic reconstruction and image orientation", by Kevin Sprague, Maria Drangova, Glen Lehmann, Piotr Slomka, David Levin, Benjamin Chow and Robert deKemp, published in Med Phys, 2006 March; 33(3):707-18;

an article titled: "A New Method of Three-dimensional Coronary Artery Reconstruction From X-Ray Angiography: Validation Against a Virtual Phantom and Multislice Computed Tomography", by Adamantios Andriotis, Ali Zifan, Manolis Gavaises, Panos Liatsis, Ioannis Pantos, Andreas Theodorakakos, Efstathios P. Efstathopoulos, and Demosthenes Katritsis, published in Catheter Cardiovasc Interv, 2008, Jan. 1; 71(1):28-43;

an article titled: "Noninvasive Measurement of Coronary Artery Blood Flow Using Combined Two-Dimensional and Doppler Echocardiography", by Kenji Fusejima, MD, published in JACC Vol. 10, No. 5, November 1987: 1024-31;

an article titled: "New Noninvasive Method for Coronary Flow Reserve Assessment: Contrast-Enhanced Transthoracic Second Harmonic Echo Doppler", by Carlo Caiati, Cristiana Montaldo, Norma Zedda, Alessandro Bina and Sabino Iliceto, published in Circulation, by the American Heart Association, 1999; 99:771-778;

an article titled: "Validation of noninvasive assessment of coronary flow velocity reserve in the right coronary artery—A comparison of transthoracic echocardiographic results with intracoronary Doppler flow wire measurements", by Harald Lethena, Hans P Triesa, Stefan Kerstinga and Heinz Lambertza, published in European Heart Journal (2003) 24, 1567-1575;

an article titled: "Coronary flow: a new asset for the echo lab?" by Paolo Vocia, Francesco Pizzutoa and Francesco Romeob, published in European Heart Journal (2004) 25, 1867-1879;

a review paper titled: "Non-invasive assessment of coronary flow and coronary flow reserve by transthoracic Doppler echocardiography: a magic tool for the real world", by Patrick Meimoun and Christophe Tribouilloy, published in European Journal of Echocardiography (2008) 9, 449-457; and an article titled: "Detection, location, and severity assessment of left anterior descending coronary artery stenoses by means of contrast-enhanced transthoracic harmonic echo Doppler", by Carlo Caiati, Norma Zedda, Mauro Cadeddu, Lijun Chen, Cristiana Montaldo, Sabino Iliceto, Mario Erminio Lepera and Stefano Favale, published in European Heart Journal (2009) 30, 1797-1806.

The disclosures of all references mentioned above and throughout the present specification, as well as the disclosures of all references mentioned in those references, are hereby incorporated herein by reference.

SUMMARY

In some embodiments of the invention, one or more models of a patient's vascular system are produced.

In some embodiments, a first model is produced from actual data collected from images of the patient's vascular system. Optionally, the actual data includes a portion of the vascular system which includes at least one blood vessel with stenosis. In these embodiments, the first model describes a portion of the vasculature system which includes at least one blood vessel with stenosis. This model is interchangeably referred to as a stenotic model. Optionally, the actual data includes a portion of the vascular system which includes at least one blood vessel with stenosis and a crown. In these embodiments the stenotic model also includes information pertaining to the shape and/or volume of the crown, and information pertaining to blood flow and/or resistance to blood flow in the crown.

In some embodiments the first model is used for calculating an index indicative of vascular function. Preferably, the index is also indicative of the potential effect of revascularization. For example, the index can be calculated based on a volume of a crown in the model and on a contribution of a stenosed vessel to the resistance to blood flow in the crown.

In some embodiments of the present invention a second model is produced from the actual data, changed so that one or more stenoses present in the patient's vascular system are modeled as if they had been revascularized.

In some embodiments the first model and the second model are compared, and the index indicative of the potential effect of revascularization is produced, based on comparing physical characteristics in the first model and in the second model.

In some embodiments the index is a Fractional Flow Reserve (FFR), as known in the art.

In some embodiments the index is some other measure which potentially correlates to efficacy of performing revascularization of one or more vessels, optionally at locations of stenosis.

According to an aspect of some embodiments of the present invention there is provided a method for vascular assessment. The method comprises, receiving a plurality of 2D angiographic images of a portion of a vasculature of a subject; and using a computer for processing the images and producing, within less than 60 minutes, a first vessel tree over a portion of the vasculature.

According to some embodiments of the invention the vasculature has therein at least a catheter other than an angiographic catheter, and wherein the images are processed and the tree is produced while the catheter is in the vasculature.

According to some embodiments of the invention the method comprises using the vascular model for calculating an index indicative of vascular function.

According to some embodiments of the invention the index is indicative of the need for revascularization.

According to some embodiments of the invention the calculation is within less than 60 minutes.

According to an aspect of some embodiments of the present invention there is provided a method of analyzing angiographic images. The method comprises: receiving a plurality of 2D angiographic images of a portion vasculature of a subject; and using a computer for processing the images to produce a tree model of the vasculature.

According to an aspect of some embodiments of the present invention there is provided a method of treating a vasculature. The method comprises: capturing a plurality of 2D angiographic images of a vascular system of a subject being immobilized on a treatment surface; and, while the subject remains immobilized: processing the images and producing a vessel tree over the vascular system; identifying a constricted blood vessel in the tree; and inflating a stent at a site of the vasculature corresponding to the constricted blood vessel in the tree.

According to some embodiments of the invention the plurality of 2D angiographic images comprise at least three 2D angiographic images, wherein the tree model is a 3D tree model.

According to some embodiments of the invention the method comprises identifying in the first vessel tree a stenosed vessel and a crown of the stenosed vessel, and calculating a resistance to fluid flow in the crown; wherein the index is calculated based on a volume of the crown, and on a contribution of the stenosed vessel to the resistance to fluid flow.

According to some embodiments of the invention the vessel tree comprises data pertaining to location, orientation and diameter of vessels at a plurality of points within the portion of the vasculature.

According to some embodiments of the invention the method comprises processing the images to produce a second three-dimensional vessel tree over the vasculature, the second vessel tree corresponding to the first vessel tree in which a stenotic vessel is replaced with an inflated vessel; wherein the calculation of the index is based on the first tree and the second tree.

According to some embodiments of the invention the method comprises processing the images to produce a second three-dimensional vessel tree over the vasculature, the second vessel tree corresponding to a portion of the vascular system which does not include a stenosis and which is geometrically similar to the first vessel tree; wherein the calculation of the index is based on the first tree and the second tree.

According to some embodiments of the invention the method comprises obtaining a Fractional Flow Ratio (FFR) based on the index.

According to some embodiments of the invention the method comprises determining, based on the index, a ratio between maximal blood flow in an area of a stenosis and a maximal blood flow in a same area without stenosis.

According to some embodiments of the invention the method comprises minimally invasively treating a stenosed vessel.

According to some embodiments of the invention the treatment is executed less than one hour from the calculation of the index.

According to some embodiments of the invention the method comprises storing the tree in a computer readable medium.

According to some embodiments of the invention the method comprises transmitting the tree to a remote computer.

According to some embodiments of the invention the method comprises capturing the 2D angiographic images.

According to some embodiments of the invention the capturing the plurality of 2D angiographic images is effected by a plurality of imaging devices to capture the plurality of 2D angiographic images.

According to some embodiments of the invention the capturing the plurality of 2D angiographic images comprises synchronizing the plurality of imaging devices to capture the plurality of images substantially at a same phase during a heart beat cycle.

According to some embodiments of the invention the synchronizing is according to the subject's ECG signal.

According to some embodiments of the invention the method comprises: detecting corresponding image features in each of N angiographic images, where N is an integer greater than 1; calculating image correction parameters based on the corresponding image features; and based on the correction parameters, registering N−1 angiographic images to geometrically correspond to an angiographic image other than the N−1 angiographic images.

According to some embodiments of the invention the method comprises defining a surface corresponding to a shape of the heart of the subject, and using the surface as a constraint for the detection of the corresponding image features.

According to some embodiments of the invention the method comprises compensating for breath and patient movement.

According to an aspect of some embodiments of the present invention there is provided a computer software product. The computer software product comprises a computer-readable medium in which program instructions are stored, which instructions, when read by a computer, cause the computer to receive a plurality of 2D angiographic images of a subject's vascular system and execute the method as delineated above and optionally as further detailed below.

According to an aspect of some embodiments of the present invention there is provided a system for vascular assessment. The system comprises: a plurality of imaging devices configured for capturing a plurality of 2D angiographic images of a vascular system of a subject; and a computer configured for receiving the plurality of 2D images and executing the method as delineated above and optionally as further detailed below.

According to an aspect of some embodiments of the present invention there is provided a system for vascular assessment comprising: a computer functionally connected to a plurality of angiographic imaging devices for capturing a plurality of 2D images of a portion of vasculature of a subject, configured to: accept data from the plurality of angiographic imaging devices; and process the images to produce a tree model of the vasculature, wherein the tree model comprises geometric measurements of the vasculature at one or more locations along a vessel of at least one branch of the vasculature.

According to some embodiments of the invention the system comprises a synchronization unit configured to provide the plurality of angiographic imaging devices with a synchronization signal for synchronizing the capturing of the plurality of 2D images of the vasculature.

According to some embodiments of the invention the computer is configured to accept a subject ECG signal, and to select, based on the ECG signal, 2D images corresponding to substantially a same phase during a heart beat cycle.

According to some embodiments of the invention the system comprises an image registration unit configured for: detecting corresponding image features in each of N angiographic images, where N is an integer greater than 1; calculating image correction parameters based on the corresponding image features; and based on the correction parameters, registering N−1 angiographic images to geometrically correspond to an angiographic image other than the N−1 angiographic images.

According to some embodiments of the invention the computer is configured for defining a surface corresponding to a shape of the heart of the subject, and using the surface as a constraint for the detection of the corresponding image features.

According to some embodiments of the invention the computer is configured for compensating for breath and patient movement.

According to some embodiments of the invention the compensating comprises iteratively repeating the detection of the corresponding image features each time for a different subset of angiographic images, and updating the image correction parameters responsively to the repeated detection of the corresponding image features.

According to some embodiments of the invention N is greater than 2. According to some embodiments of the invention N is greater than 3.

According to some embodiments of the invention the corresponding image features comprise at least one of a group consisting of an origin of the tree model, a location of minimal radius in a stenosed vessel, and a bifurcation of a vessel.

According to some embodiments of the invention the tree model comprises data pertaining to location, orientation and diameter of vessels at a plurality of points within the portion of the vasculature.

According to some embodiments of the invention tree model comprising measurements of the vasculature at one or more locations along at least one branch of the vasculature.

According to some embodiments of the invention the geometric measurements of the vasculature are at one or more locations along a centerline of at least one branch of the vasculature.

According to some embodiments of the invention the tree model comprises data pertaining to blood flow characteristics in at one or more of the plurality of points.

According to some embodiments of the invention the portion of the vasculature comprises the heart arteries.

According to an aspect of some embodiments of the present invention there is provided a method for vascular assessment comprising: receiving a plurality of 2D angiographic images of a portion of a vasculature of a subject, and processing the images to produce a stenotic model over the vasculature, the stenotic model having measurements of the vasculature at one or more locations along vessels of the vasculature; obtaining a flow characteristic of the stenotic model; and calculating an index indicative of vascular function, based, at least in part, on the flow characteristic in the stenotic model.

According to some embodiments of the invention the flow characteristic of the stenotic model comprises resistance to fluid flow.

According to some embodiments of the invention the method comprises identifying in the first stenotic model a stenosed vessel and a crown of the stenosed vessel, and calculating the resistance to fluid flow in the crown; wherein the index is calculated based on a volume of the crown, and on a contribution of the stenosed vessel to the resistance to fluid flow.

According to some embodiments of the invention the flow characteristic of the stenotic model comprises fluid flow.

According to some embodiments of the invention the stenotic model is a three-dimensional vessel tree.

According to some embodiments of the invention the vessel tree comprises data pertaining to location, orientation and diameter of vessels at a plurality of points within the portion of the vasculature.

According to some embodiments of the invention the processing comprises: extending the stenotic model by one bifurcation; calculating a new flow characteristic in the extended stenotic model; updating the index responsively to the new flow characteristic and according to a predetermined criterion; and iteratively repeating the extending, the calculating and the updating.

According to some embodiments of the invention the method comprises processing the images to produce a second model over the vasculature, and obtaining a flow characteristic of the second model; wherein the calculation of the index is based on the flow characteristic in the stenotic model and on the flow characteristic in the second model.

According to some embodiments of the invention the second model is a normal model, comprising an inflated vessel replacing a stenotic vessel in the stenotic model.

According to some embodiments of the invention the stenotic model is a three-dimensional vessel tree and the second model is a second three-dimensional vessel tree.

According to some embodiments of the invention each of the models corresponds to a portion of the vasculature which is between two consecutive bifurcations of the vasculature and which includes a stenosis.

According to some embodiments of the invention each of the models corresponds to a portion of the vasculature which includes a bifurcation of the vasculature.

According to some embodiments of the invention each of the models corresponds to a portion of the vasculature which includes a stenosis and which extends at least one bifurcation of the vasculature beyond the stenosis.

According to some embodiments of the invention the each of the models corresponds to a portion of the vasculature which includes a stenosis and which extends at least three bifurcations of the vasculature beyond the stenosis.

According to some embodiments of the invention the method wherein each of the models corresponds to a portion of the vasculature which includes a stenosis and which extends distally as far as resolution of the images allows.

According to some embodiments of the invention the stenotic model corresponds to a portion of the vasculature which includes a stenosis, and the second model corresponds to a portion of the vasculature which does not include a stenosis and which is geometrically similar to the stenotic model.

According to some embodiments of the invention the processing comprises: extending each of the models by one bifurcation; calculating a new flow characteristic in each extended model; updating the index responsively to the new flow characteristics and according to a predetermined criterion; and iteratively repeating the extending, the calculating and the updating.

According to some embodiments of the invention the index is calculated based on a ratio of the flow characteristic in the stenotic model to the flow characteristic in the second model.

According to some embodiments of the invention the index is indicative of the need for revascularization.

According to an aspect of some embodiments of the present invention there is provided a method for vascular assessment including producing a stenotic model of a subject's vascular system, the stenotic model including measurements of the subject's vascular system at one or more locations along a vessel centerline of the subject's vascular system, obtaining a flow characteristic of the stenotic model, producing a second model, of a similar extent of the subject's vascular system as the stenotic model, obtaining the flow characteristic of the second model, and calculating an index indicative of the need for revascularization, based on the flow characteristic in the stenotic model and on the flow characteristic in the second model.

According to some embodiments of the invention, the second model is a normal model, including an inflated vessel replacing a stenotic vessel in the stenotic model.

According to some embodiments of the invention, the vascular system includes the subject's heart arteries.

According to some embodiments of the invention, the producing a stenotic model of a subject's vascular system includes using a plurality of angiographic imaging devices for capturing a plurality of 2D images of the subject's vascular system, and producing the stenotic model based on the plurality of 2D images.

According to some embodiments of the invention, the flow characteristic includes fluid flow.

According to some embodiments of the invention, the obtaining the flow characteristic of the stenotic model includes measuring fluid flow in the subject's vascular system at the one or more locations in the extent of the subject's vascular system included in the stenotic model, and the obtaining the flow characteristic of the second model includes calculating fluid flow in the subject's vascular system at the one or more locations in the extent of the subject's vascular system included in the second model, based, at least in part, on correcting the fluid flow of the stenotic model to account for an inflated vessel.

According to some embodiments of the invention, the flow characteristic includes resistance to fluid flow.

According to some embodiments of the invention, the obtaining the flow characteristic of the stenotic model includes calculating a resistance to flow based, at least in part, on the subject vascular system cross sectional area at the one or more locations in the extent of the subject's vascular system included in the stenotic model, and obtaining the flow characteristic of the second model includes calculating the resistance to flow based, at least in part, on the subject vascular system inflated cross sectional area at the one or more locations in the extent of the subject's vascular system included in the second model.

According to some embodiments of the invention, the extent of each one of the stenotic model and the second model includes a segment of the vascular system, between two consecutive bifurcations of the vascular system, which includes a stenosis.

According to some embodiments of the invention, the extent of each one of the stenotic model and the second model includes a segment of the vascular system which includes a bifurcation of the vascular system.

According to some embodiments of the invention, each one of the stenotic model and the second model include an extent of the vascular system which includes a stenosis and extends at least one bifurcation of the vascular system beyond the stenosis.

According to some embodiments of the invention, each one of the stenotic model and the second model include an extent of the vascular system which includes a stenosis and an inflated stenosis respectively and extends at least three bifurcations of the vascular system beyond the stenosis.

According to some embodiments of the invention, each one of the stenotic model and the second model include an extent of the vascular system which includes a stenosis and extends distally as far as resolution of an imaging modality allows.

According to some embodiments of the invention, each one of the stenotic model and the second model include an extent of the vascular system which includes a stenosis and extends distally at least one bifurcation of the vascular system beyond the stenosis, and further including storing the flow characteristic of the stenotic model as a previous flow characteristic of the stenotic model and storing the flow characteristic of the second model as a previous flow characteristic of the second model, extending the extent of the stenotic model and the second model by one more bifurcation, calculating a new flow characteristic in the stenotic model and calculating a new flow characteristic in the second model, deciding whether to calculate the index indicative of the need for revascularization as follows: if the new flow characteristic of the stenotic model differs from the previous characteristic of the stenotic model by less than a first specific difference, and the new flow characteristic of the second model differs from the previous characteristic of the second model by less than a second specific difference, then calculating the index indicative of the need for revascularization, else repeating the storing, the extending, the calculating, and the deciding.

According to some embodiments of the invention, the stenotic model includes an extent of the vascular system which includes a stenosis, the second model includes an extent of the vascular system which does not include a stenosis and which is geometrically similar to the first model.

According to some embodiments of the invention, the index is calculated as a ratio of the flow characteristic in the stenotic model to the flow characteristic in the second model.

According to some embodiments of the invention, the calculated index is used to determine a Fractional Flow Ratio (FFR).

According to some embodiments of the invention, the calculated index is used to determine a ratio between maximal blood flow in an area of stenosis and a maximal blood flow in a same area without stenosis.

According to some embodiments of the invention, the producing a stenotic model, the obtaining a flow characteristic of the stenotic model, the producing a second model, the obtaining the flow characteristic of the second model, and the calculating an index, are all performed during a diagnostic catheterization, before a catheter used for the diagnostic catheterization is withdrawn from the subject's body.

According to an aspect of some embodiments of the present invention there is provided a method for vascular assessment including capturing a plurality of 2D angiographic images of a subject's vascular system, producing a tree model of the subject's vascular system, the tree model including geometric measurements of the subject's vascular system at one or more locations along a vessel centerline of at least one branch of the subject's vascular system, using at least some of the plurality of captured 2D angiographic images, and producing a model of a flow characteristic of the first tree model.

According to some embodiments of the invention, the vascular system includes the subject's heart arteries.

According to some embodiments of the invention, the capturing a plurality of 2D angiographic images includes using a plurality of imaging devices to capture the plurality of 2D angiographic images.

According to some embodiments of the invention, the capturing a plurality of 2D angiographic images includes synchronizing the plurality of imaging devices to capture the plurality of images at a same moment.

According to some embodiments of the invention, the synchronizing uses the subject's ECG signal.

According to some embodiments of the invention, the synchronizing includes detecting corresponding image features in at least a first 2D angiographic image and a second 2D angiographic image of the plurality of 2D angiographic images, calculating image correction parameters based on the corresponding image features, and registering at least the second 2D angiographic image to geometrically correspond to the first 2D angiographic image, wherein the corresponding image features include at least one of a group consisting of an origin of the tree model, a location of minimal radius in a stenosed vessel, and a bifurcation of a vessel.

According to an aspect of some embodiments of the present invention there is provided a system for vascular assessment including a computer functionally connected to a plurality of angiographic imaging devices for capturing a plurality of 2D images of a patient's vascular system, configured to accept data from the plurality of angiographic imaging devices, produce a tree model of the subject's vascular system, wherein the tree model includes geometric measurements of the subject's vascular system at one or more locations along a vessel centerline of at least one branch of the subject's vascular system, using at least some of the plurality of captured 2D images, and produce a model of flow characteristics of the tree model.

According to some embodiments of the invention, the vascular system includes the subject's heart arteries.

According to some embodiments of the invention, further including a synchronization unit configured to provide the plurality of angiographic imaging devices with a synchronization signal for synchronizing the capturing of the plurality of 2D images of the subject's vascular system.

According to some embodiments of the invention, further including a synchronization unit configured to accept a subject ECG signal, and to select 2D images from the data from the plurality of angiographic imaging devices at a same cardiac phase in the 2D images.

According to some embodiments of the invention, further including an image registration unit configured to detect corresponding image features in at least a first 2D image and a second 2D image from the data from the plurality of angiographic imaging devices, to calculate image correction parameters based on the corresponding image features, and to register at least the second 2D image to geometrically correspond to the first 2D image, wherein the corresponding image features include at least one of a group consisting of an origin of the tree model, a location of minimal radius in a stenosed vessel, and a bifurcation of a vessel.

According to an aspect of some embodiments of the present invention there is provided a method for vascular assessment including producing a stenotic model of a subject's vascular system, the stenotic model including geometric measurements of the subject's vascular system at one or more locations along a vessel centerline of the subject's vascular system, including an extent of the vascular system which includes a stenosis and extends at least one bifurcation of the vascular system beyond the stenosis, obtaining a flow characteristic of the stenotic model, producing a second model, of a similar extent of the subject's vascular system as the stenotic model, obtaining the flow characteristic of the second model, and calculating an index indicative of the need for revascularization, based on the flow characteristic in the stenotic model and on the flow characteristic in the second model, and further including storing the flow characteristic of the stenotic model as a previous flow characteristic of the stenotic model and storing the flow characteristic of the second model as a previous flow characteristic of the second model, extending the extent of the stenotic model and the second model by one more bifurcation, calculating a new flow characteristic in the stenotic model and calculating a new flow characteristic in the second model, deciding whether to calculate the index indicative of the need for revascularization as follows: if the new flow characteristic of the stenotic model differs from the previous characteristic of the stenotic model by less than a first specific difference, and the new flow characteristic of the second model differs from the previous characteristic of the second model by less than a second specific difference, then calculating the index indicative of the need for revascularization, else repeating the storing, the extending, the calculating, and the deciding.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 depicts a coronary tree model, a combination matrix depicting tree branch tags, and a combination matrix depicting tree branch resistances, all produced according to an example embodiment of the invention;

FIG. 6 depicts a tree model of a vascular system, with tags numbering outlets of the tree model, produced according to an example embodiment of the invention, the tags corresponding to stream lines;

DETAILED DESCRIPTION

Figure 1:
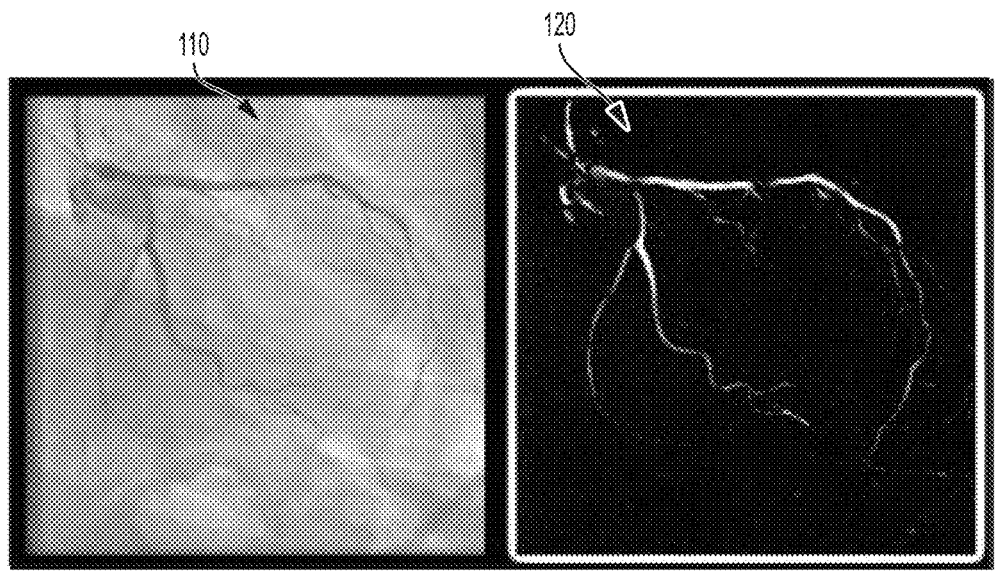
FIG. 1 depicts an original image and a Frangi-filter processed image, processed according to an example embodiment of the invention.

The present invention, in some embodiments thereof, relates to vascular flow assessment and, more particularly, but not exclusively, to modeling vascular flow and to assessing vascular flow.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

It is noted that in example embodiments described below, the coronary vessel system, and more specifically the coronary artery system, is used. The example is not meant to limit embodiments of the invention to the coronary arteries, as embodiments of the invention potentially apply to other vessel systems, such as, for example, the vein system and the lymph system.

In some embodiments, a first model of vascular flow in a subject, based on imaging the subject's vascular system, is constructed. Typically, the first model is constructed of a vascular system which includes a problem section of the vascular system, such as a stenosis in at least part of a vessel. In some embodiments of the present invention the first model corresponds to a portion the vascular system which includes at least one blood vessel with stenosis. In these embodiments, the first model describes a portion of the vasculature system which includes at least one blood vessel with stenosis and a crown. In these embodiments the first model optionally and preferably includes information pertaining to the shape and/or volume of the crown, and information pertaining to blood flow and/or resistance to blood flow in the stenosed blood vessel and/or the crown.

Typically, but not necessarily, a second model is constructed. The second model optionally and preferably describes a healthy vascular system corresponding to the first model. In some embodiments the second model is constructed by changing a stenosis in the first model to be more open, as it would be if a stent were to open the stenosis; and in some embodiments the second model is constructed by choosing a section of the subject's vascular system which includes a healthy vessel similar to the problem vessel of the first model.

Various ways of constructing the models are described below in more detail.

In some embodiments, an index indicative of the need for revascularization is calculated. This can be done based on the first model or based on a comparison between the first and the second models of the vascular flow. The index is optionally used similarly to the FFR index, to assess whether a stenosed vessel affects flow in the vascular system to such an extent that the prognosis for improvement in the subject's condition following inflation of the stenosed vessel, is higher than the likelihood for complications resulting from the inflation itself.

The terms "FFR" and "FFR index" in all their grammatical forms are used throughout the present specification and claims to stand for the above-mentioned index, and not only for the FFR index mentioned in the Background section as an invasive measurement involving insertion of a guidewire equipped with a miniature pressure transducer across the stenosis.

Acquiring Data for Constructing a Vascular Model

Data for modeling a vascular system may be collected from various sources.

In some embodiments, the data is from minimally invasive angiographic images. In some embodiments, the angiographic images are two-dimensional, and data from more than one angiographic image, taken from different viewing angles, is optionally used to produce a model which includes three-dimensional data inferred from the two-dimensional angiographic images taken from the different viewing angles.

In some embodiments, the data is from computerized tomography (CT) scans.

It is noted that under present day technology, angiographic images provide a finer resolution than CT scans. Models of the vascular system constructed based on angiographic images, whether 1D tree models or full 3D models, are potentially more accurate than models based on CT scans, and potentially provide a more accurate vascular assessment.

Constructing a Vascular Model

In some embodiments, the vascular system model is a tree model, optionally and preferably a three-dimensional tree model.

The tree model is a tree data structure having nodes linked by curvilinear segments. The nodes are associated with vascular furcations (e.g., bifurcation or trifurcations or multi-furcations), and the curvilinear segments are associated with vessel segments. A curvilinear segment of the tree is referred to below as a branch, and the entire tree portion distal to a branch is referred as a crown.

Thus, tree model describes the vascular system by assigning nodes of the tree to vascular furcations and branches of the tree to vessel segments of the vascular system.

In some embodiments, the tree model may be represented by a series of disks or poker chips (e.g., circular or elliptical disks) that are linked together to form a three-dimensional structure containing information relating to the local size, shape, branching, and other structural features at any point in the vascular tree.

In some embodiments, trifurcations and/or multi-furcations are methodically converted to a combination of bifurcations. For example a trifurcation is optionally converted to two bifurcations. The term "bifurcation" in all its grammatical forms is used throughout the present specification and claims to mean bifurcation, trifurcation, or multi-furcation.

In some embodiments the tree model includes data describing several specific points along each branch in the model. In some embodiments, data associated with branches of the tree includes geometrical properties of the vessel at the branch, or at a specific point of the branch. In some embodiments, the geometrical properties include location, orientation and diameter of vessels at a plurality of points within a portion of the vasculature. The geometrical properties can also include a cross sectional area of the vessel at the specific point, and/or a radius of the vessel at the specific point. The tree model can also comprise flow characteristics at one or more of the points.

In some embodiments the tree model is produced using geometric data measured along vessel centerlines of a vascular system.

In some embodiments, the vascular system model is a three-dimensional model, for example a three-dimensional model as may be obtained from a CT scan, and/or as may be constructed from a set of two-dimensional angiographic images taken from different angles.

In some embodiments, the vascular system model is a one-dimensional model, modeling segments of vessels as lines, which are one-dimensional, along center lines of a set of vessels of a vascular system.

In some embodiments, the one-dimensional model is a tree model of the vascular system, including data about segments which includes where a segment splits into two or more segments along a vessel.

In some embodiments the model includes a collection of data along segments of the vessels, including three dimensional data associated with a one-dimensional collection of points—for example, data about a cross sectional area at each point, and/or data about a three-dimensional direction of a segment, and/or data about an angle of bifurcation, and so on.

In some embodiments, the model of the vascular system is used to calculate a physical model of fluid flow, including physical characteristics such as pressure and/or flow rate, and/or flow resistance, and/or shear stress, and/or flow velocity.

It is noted that performing calculations for a one-dimensional collection of points, such as calculations of resistance to fluid flow, is potentially much more efficient than performing such calculations using a full three-dimensional model which includes all voxels of a vascular system.

A preferred procedure for producing a tree model is as follows. Corresponding image features are identified in each of a plurality of angiographic images (e.g., in each captured image). An image feature can be, for example, a furcation of a vessel, a location of minimal radius in a stenosed vessel, and the like. In some embodiments of the present invention, a surface corresponding to a shape of the heart of the subject is defined. This surface is optionally and preferably used as a constraint for the detection of the corresponding image features. Such a surface can be defined using any technique known in the art, including, without limitation, polyhedra stitching.

Image correction parameters can then be calculated based on the identified corresponding image features. The correction parameters typically describe translation and/or rotation of the system of coordinates for a particular image. Based on the calculated parameters, the angiographic images are registered to provide mutual geometrically correspondence thereamongst. Typically, several images are registered relative to one of the images. For example, when corresponding image features are identified in N images (e.g., N=2, 3, 4 or more) one of the images can be selected as a reference, while the registration is applied for the remaining N−1 angiographic images such that each of those remaining images geometrically corresponds to the single angiographic image that was selected as a reference. Other registration scenarios (e.g., pairwise registration) are not excluded from the scope of the present invention.

In various exemplary embodiments of the invention the procedure compensates for breath and patient movement. This is optionally and preferably done by iteratively repeating the detection of the corresponding image features, each time for a different subset of angiographic images, and updating the image correction parameters responsively to the repeated detection. For example, in each iteration, a subset of the centerlines is analyzed to provide a three-dimensional volume occupied by the subset of centerlines. The skeleton of this volume can then be computed and project on one or more of the remaining 2D images that were not included in the analysis. The image correction parameters of these remaining images are then updated so as to reduce the offset between the projected line and the centerline in the 2D image. It was found by the present inventors that such an iterative process significantly reduces the effects of breath, patient movements, and heart phase difference.

The computational procedure of the present embodiments is simpler than conventional techniques which employ computational fluid dynamics simulation and analysis. It is recognized that computational fluid dynamics require substantial computation power and/or time. For example, several days CPU times are required when fluid dynamics simulation is executed on a standard PC. While this time can be somewhat reduced using a super-computer applying parallel processing, such a computation platform is hardly available in medical facilities. The computational procedure of the present embodiments is not based on fluid dynamic simulations and can therefore be implemented on a standard computing platform, without the need for a super-computer.

The present inventors found that a tree model according to some embodiments of the present invention can be provided within less than 60 minutes or less than 50 minutes or less than 40 minutes or less than 30 minutes or less than 20 minutes from the time at which the 2D images are received by the computer. This allows the present embodiments to efficiently combine between the computation and treatment, wherein the tree model is optionally and preferably produced while the subject is immobilized on a treatment surface (e.g., a bed) for the purpose of catheterization. In some embodiments of the present invention the tree model is produced while the subject has a catheter in his or her vasculature. In some embodiments of the present invention the vasculature has at least one catheter other than an angiographic catheter, (e.g., a cardiac catheter or an intracranial catheter), wherein the images are processed and the tree is produced while the catheter is in the vasculature.

Vascular Assessment

In some embodiments of the present invention the stenotic model is used for calculating an index indicative of vascular function. The index can also be indicative of the need for revascularization. A representative example of an index suitable for the present embodiments includes, without limitation, FFR.

In some embodiments, the index is calculated based on a volume of a crown in the stenotic model and on a contribution of a stenosed vessel to the resistance to blood flow in the crown. In some embodiments, the FFR index is calculated as a ratio of flow resistance of a stenosed vessel in a vascular model which includes the stenosed vessel to flow resistance of an inflated version of the same vessel in a similar vascular model where the stenosed vessel was mathematically inflated.

In some embodiments, the index is calculated as a ratio of flow resistance of a stenosed vessel in a vascular model to flow resistance of a neighboring similar healthy vessel in the vascular model. The ratio may be multiplied by a constant which accounts for different geometries of the stenosed vessel and the neighboring vessel, as described below in the section titled "Producing a model of physical characteristics of a vascular system".

In some embodiments, a first tree model of a vascular system is produced, based on actual patient measurements, optionally containing a stenosis in one or more locations of the patient's vessels, and a second tree model of the patient's vascular system is produced, optionally changed so that at least one of the stenosis locations is modeled as after revascularization, and an index indicative of the need for revascularization is produced, based on comparing physical characteristics of the first model and the second model.

In some embodiments, actual pressure and/or flow measurements are used to calculate the physical characteristics in the model(s) and/or the above-mentioned index.

In some embodiments, no actual pressure and/or flow measurements are used to calculate the physical characteristics in the model(s) and/or the above-mentioned index.

It is noted that resolution of angiographic images is typically higher than resolution typically obtained by 3D techniques such a CT. A model constructed from the higher resolution angiographic images, according to some embodiments, can be inherently higher resolution, and provide greater geometric accuracy, and/or use of geometric properties of smaller vessels than CT images, and/or calculations using branching vessels distal to a stenosis for more generations, or bifurcations, downstream from the stenosis than CT images.

Producing a Geometric Model of a Vascular System

Some example embodiments of methods for producing a geometric model of a vascular system are now described.

One example embodiment of a method for producing a geometric model of a vascular system includes producing a 3D model representing a vascular system, such as, by way of a non-limiting example, a coronary tree of the vascular system, from a set of 2D angiography images.

Reference is now made to FIG. 1, which depicts an original image 110 and a Frangi-filter processed image 120, processed according to an example embodiment of the invention.

The original image 110 depicts a typical angiogram 2D image.

In some embodiments, the original image 110 is further processed to enhance and detect vessels in the original image 110. By way of a non-limiting example, the Frangi-filter processed image 120 depicts the original image 110 after image enhancement using a Frangi filter. In some embodiments, vessel center-lines are determined for the angiograms and/or for the vessel-enhanced angiograms.

Figure 2:
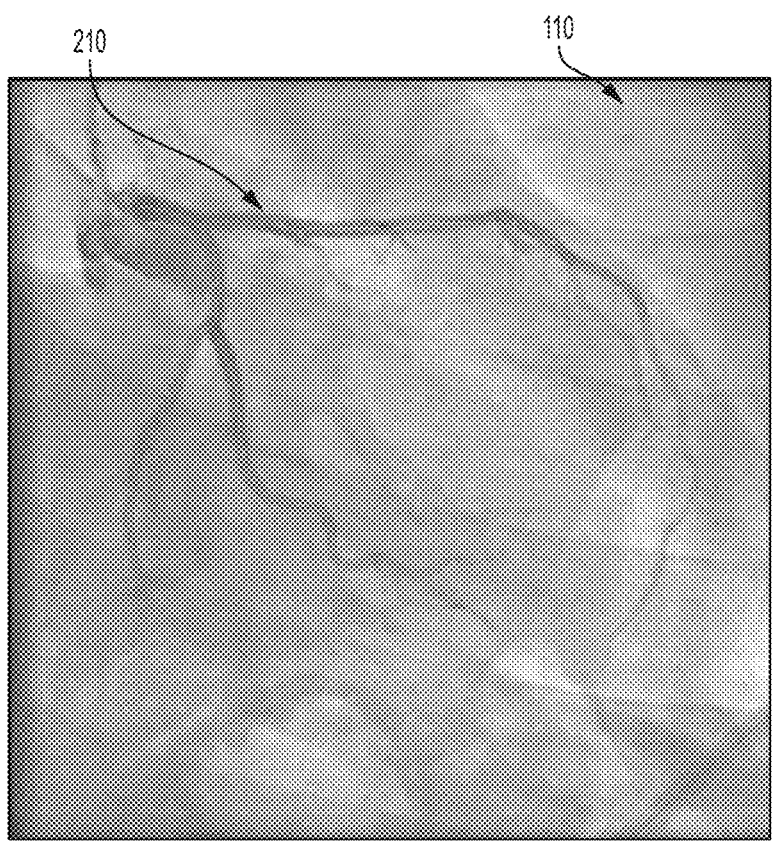
FIG. 2 depicts a light-colored center line overlaid on top of the original image of FIG. 1, according to an example embodiment of the invention.

Reference is now made to FIG. 2, which depicts a light-colored center line 210 overlaid on top of the original image 110 of FIG. 1, according to an example embodiment of the invention.

The example method for producing a geometric model of a vascular system optionally includes extracting vessel center-lines from at least two 2D projections, identifying homologous vessels in the different projections, and applying epipolar geometry methods to obtain a 3D model of the coronary tree.

In some embodiments, the three dimensional model is optionally thinned to produce a coronary vessel tree, as will be further described below with reference to FIGS. 3A, 3B and 3C.

In some embodiments, the coronary vessel tree includes a set of points, each of which may be a bifurcation or multi-furcation point in a tree, or a point along a branch of the tree.

In some embodiments, the three dimensional model is optionally used to estimate a diameter of the vessels.

In some embodiments, diameters of the vessels are recorded corresponding to at least some of the various points in the set of points are included in the coronary vessel tree.

Motion Compensation

It is noted that when using two or more 2D projections of a subject's vessels, for example heart vessels, it may be desirable that the two or more 2D projections be taken at the same time, or at least at a same phase during a heart beat cycle, so that the 2D projections be of a same vessel shape.

Deviations between the 2D projections might arise from cardiac, and/or respiratory and/or patient motions between the 2D projection frames.

In some embodiments, to minimize deviations that might arise from lack of cardiac phase synchronization, an ECG output is used to choose a same cardiac phase in the 2D projections frames. Optionally, an ECG output is recorded with a time scale, and a corresponding time scale is used to record when images of the vascular system are captured.

In some embodiments 2D projection frames are selected to be at an end of the diastole phase of the cardiac cycle.

In some embodiments the heart is imaged under influence of intravenous adenosine, which may exaggerate a difference between normal and abnormal segments.

In some embodiments, to compensate for respiratory and patient motions, features are identified in the 2D projections. The features optionally include an origin of the coronary vessel tree, and/or points of minimal radius in sick vessels, and/or bifurcations. The features optionally act as anchors to correct the coronary vessel tree position in space.

In some embodiments, the features are optionally also used to align images taken from different directions, or even used only for alignment of images taken from different directions.

In some embodiments, to perform the correction, epipolar geometry is used to compute shift and/or rotation and/or expansion parameters which result in a best fit between the anchors.

Construction of a Vessel Tree Model

After reconstruction of a vessel tree model, such as a coronary tree, from angiographic images, the tree model is optionally divided into branches, where a branch is defined as a section of a vessel between bifurcations. The branches are numbered according to their generation in the tree.

Figure 3C:
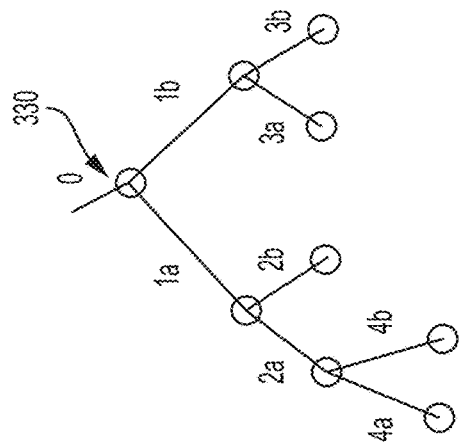
FIG. 3C is a simplified illustration of a tree model of a coronary vessel tree, produced according to an example embodiment of the invention.
Figure 3B:
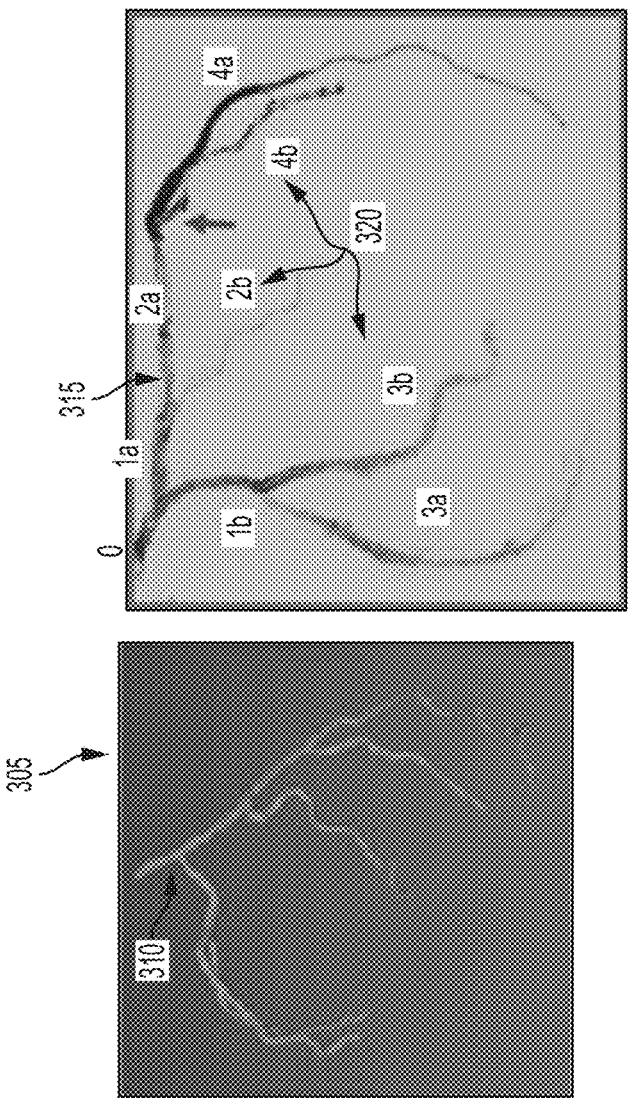
FIG. 3B is an image of a coronary vessel tree model of FIG. 3A, with tree branch tags added according to an example embodiment of the invention.
Figure 3A:
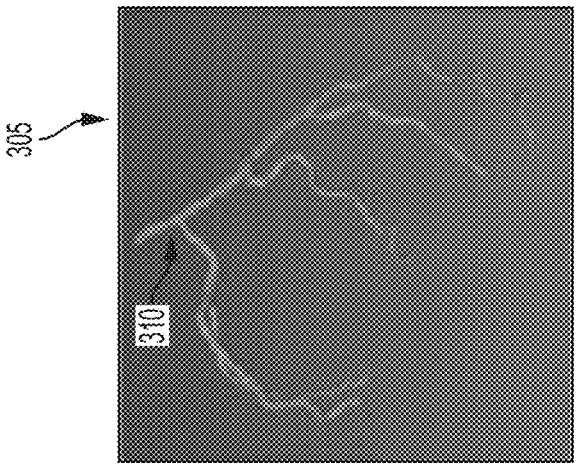
FIG. 3A is an image of a coronary vessel tree model, produced according to an example embodiment of the invention.

Reference is now made to FIG. 3A, which is an image 305 of a coronary vessel tree model 310, produced according to an example embodiment of the invention.

Reference is now also made to FIG. 3B, which is an image of a coronary vessel tree model 315 of FIG. 3A, with tree branch tags 320 added according to an example embodiment of the invention.

It is noted that the tags 320 are simply one example method for keeping track of branches in a tree model.

Reference is now also made to FIG. 3C, which is a simplified illustration of a tree model 330 of a coronary vessel tree, produced according to an example embodiment of the invention.

In some embodiments, the tree model is represented by a one-dimensional array. For example, the 9-branch tree in FIG. 3C is represented by a 9-element array: a=[0 1 1 2 2 3 3 4 4], which lists tree nodes in a breadth-first order.

In some embodiments, during a reconstruction process, spatial location and radius of segments on each branch are sampled every small distance, for example every 1 mm, or every 0.1 mm to every 5 mm.

In some embodiments, tree branches, corresponding to vessel segments between modeled bifurcations, correspond to vessel segments of a length of 1 mm, 5 mm, 10 mm, 20 mm, 50 mm, and even longer.

In some embodiments, sampling every small distance increases the accuracy of a geometric model of the vessels, thereby increasing accuracy of flow characteristics calculated based on the geometric measurements.

In some embodiments, the tree model may be a minimal tree, limited to a single segment of a vessel, between two consecutive bifurcations of the vascular system.

Measuring Flow from Time Intensity Curves in Angiographic Sequences

In some embodiments, a physical model of fluid flow in the coronary vessel tree is calculated, including physical characteristics such as pressure and/or flow rate, and/or flow resistance, and/or shear stress, and/or flow velocity.

In an example embodiment, a techniques based on the analysis of concentration-distance-time curves is used. The techniques perform well in conditions of pulsatile flow. An example concentration-distance-time curve technique is the concentration-distance curve matching algorithm.

Using the above-mentioned technique, a concentration of contrast material, such as iodine, present at a particular distance along a vessel segment, is found by integrating pixel intensities in angiogram(s) across a vessel lumen perpendicular to the centerline. An optimal shift is found in a distance axis between consecutive concentration-distance curves. A blood flow velocity is then calculated by dividing the shift by the time interval between the curves. Several variations of the above technique have been reported in the following references, the contents of which are hereby incorporated herein by reference: The four above-mentioned articles by Seifalian et al; the above-mentioned article titled: "Determination of instantaneous and average blood flow rates from digital angiograms of vessel phantoms using distance-density curves", by Hoffmann et al; the above-mentioned article titled: "Comparison of methods for instantaneous angiographic blood flow measurement", by Shpilfoygel et al; and the article titled: "Quantitative angiographic blood flow measurement using pulsed intra-arterial injection", by Holdsworth et al.

Measuring Flow Using Other Modalities

In some embodiments flow is calculated from ultrasound measurements. Several variations of the above mentioned ultrasound technique have been reported in above-mentioned references, the contents of which are hereby incorporated herein by reference: the above-mentioned article titled: "Noninvasive Measurement of Coronary Artery Blood Flow Using Combined Two-Dimensional and Doppler Echocardiography", by Kenji Fusejima; the article titled: "New Noninvasive Method for Coronary Flow Reserve Assessment: Contrast-Enhanced Transthoracic Second Harmonic Echo Doppler", by Carlo Caiati et al; the article titled: "Validation of noninvasive assessment of coronary flow velocity reserve in the right coronary artery—A comparison of transthoracic echocardiographic results with intracoronary Doppler flow wire measurements", by Harald Lethena et al; the article titled: "Coronary flow: a new asset for the echo lab?" by Paolo Vocia et al; the review paper titled: "Non-invasive assessment of coronary flow and coronary flow reserve by transthoracic Doppler echocardiography: a magic tool for the real world", by Patrick Meimoun et al; and the article titled: "Detection, location, and severity assessment of left anterior descending coronary artery stenoses by means of contrast-enhanced transthoracic harmonic echo Doppler", by Carlo Caiati et al.

In some embodiments, other modalities of measuring flow in the coronary vessel tree are used. Example modalities include MRI flow measurement and SPECT (Single-photon emission computed tomography), or gamma camera, flow measurement.

It is noted that in some embodiments a vascular flow model is constructed without using flow measurements or pressure measurements, based on geometrical measurement taken from images of the vascular system.

It is noted that in some embodiments flow measurements are used to verify flow characteristics calculated based on a model constructed based on the geometric measurements.

It is noted that in some embodiments pressure measurements are used to verify flow characteristics calculated based on a model constructed based on the geometric measurements.

An Example Embodiment of Producing a Model in which Stenoses are Modeled as if they had been Revascularized—Stenosis Inflation In some embodiments an estimation is made of a structure of a sick vessel as if the vessel has been revascularized to a healthy structure. Such a structure is termed an inflated structure—as if a stenosed vessel has been revascularized back to normal diameter.

In some embodiments a technique is used as described in the following references, the contents of which are hereby incorporated herein by reference: the article titled "Dedicated bifurcation analysis: basic principles", by Tuinenburg et al; the article titled "Quantitative Coronary Angiography in the Interventional Cardiology", by Tomasello et al; and the article titled "New approaches for the assessment of vessel sizes in quantitative (cardio-)vascular X-ray analysis", by Janssen et al.

A stenosis inflation procedure is optionally implemented for each one of the 2D projections separately. In some cases a stenosis may occur in a region nearby to a bifurcation and in some cases the stenosis may occur along a vessel. The stenosis inflation procedure in the two cases is now described separately.

If the stenosis is not located at a bifurcation region, it is enough to assess flow in the sick vessel. Coronary vessel segments proximal and distal to the stenosis are relatively free of disease and are referred to as reference segments. An algorithm optionally calculates a coronary edge by interpolating the coronary vessel segments considered free from illness located proximally and distally to the region of stenosis with the edges of the region of the stenosis. The algorithm optionally reconstructs a reference coronary segment that is as if free from disease.

In some embodiments the technique includes calculation of a mean value of the diameters of a vessel lumen in the segment of reference located upstream and downstream to the lesion.

If the stenosis is located at a bifurcation region, two example bifurcation models are defined: a T-shape bifurcation model and a Y-shape bifurcation model.

The bifurcation model, T-shape or Y-shape, is optionally detected by analyzing arterial contours of three vessel segments connected to the bifurcation. Calculation of a flow model for an inflated healthy vessel diameter is based on calculating as if each of the three segments connected to the bifurcation has a healthy diameter. Such a calculation ensures that both a proximal and a distal main (interpolated) reference diameter are based on arterial diameters outside the bifurcation core.

A reference diameter function of a bifurcation core is optionally based on a reconstruction of a smooth transition between the proximal and the distal vessel diameters. As a result, the reference diameter of the entire main section can be displayed as one function, composed of three different straight reference lines linked together.

An Example of Producing a Model of Physical Characteristics of a Vascular System Some example embodiments of methods for producing a model of physical characteristics of a vascular system are now described.

An example vascular system which will be used in the rest of the description below is the coronary vascular system.

In some embodiments of the invention, in order to evaluate an FFR index in a stenosed branch of a vessel tree, a one dimensional model of the vessel tree is used to estimate the flow in the stenosed branch before and optionally also after stent implantation.

In some embodiments of the invention, in order to evaluate an FFR index in a stenosed branch of a vessel tree, a one dimensional model of the vessel tree is used to estimate the flow in the stenosed branch before and optionally also after stenosis inflation.

Based on maximal peak flow of 500 mL/min and artery diameter of 5 mm, a maximal Reynolds number of the flow is:

$$Re_{peak\_Flow} = \frac{4Q_{peak\_flow}}{\pi d_{max} v} = \frac{4 \cdot 500_{mL/min}}{\pi \cdot 5_{min} \cdot 3.5_{cP}} \approx 600 \quad \text{Equation 5.1}$$

The above calculation assumes laminar flow. In laminar flow it is assumed, for example, that blood is a Newtonian and homogenous fluid. Another assumption which is optionally made is that flow in vessel branches is one-dimensional and fully developed across the cross section of the vessel.

Based on the assumptions, a pressure drop in each segment of a vessel tree is approximated according to Poiseuille formulation in straight tubes:

$$\Delta P_i = \frac{128 \mu L_i}{\pi d_i^4} Q_i = \mathfrak{R}_i Q_i \quad \text{Equation 5.2}$$

Where $\mathfrak{R}_i$ is a viscous resistance to flow of a segment of the vessel. Minor losses, due to bifurcations, constrictions and curvatures of the vessels are optionally added as additional resistances in series, according to the Darcy-Weisbach formulation:

$$\Delta p = \frac{\rho V^2}{2} \cdot \sum K_i = \frac{8 \rho Q^2}{\pi^2 d^4} \cdot \sum K_i \quad \text{Equation 5.3}$$

$$\mathfrak{R}(Q) = \frac{\Delta p}{Q} = \left( \frac{8\rho}{\pi^2 d^4} \cdot \sum K_i \right) Q \quad \text{Equation 5.4}$$

where $K_i$ are corresponding loss coefficients.

Figure 4:
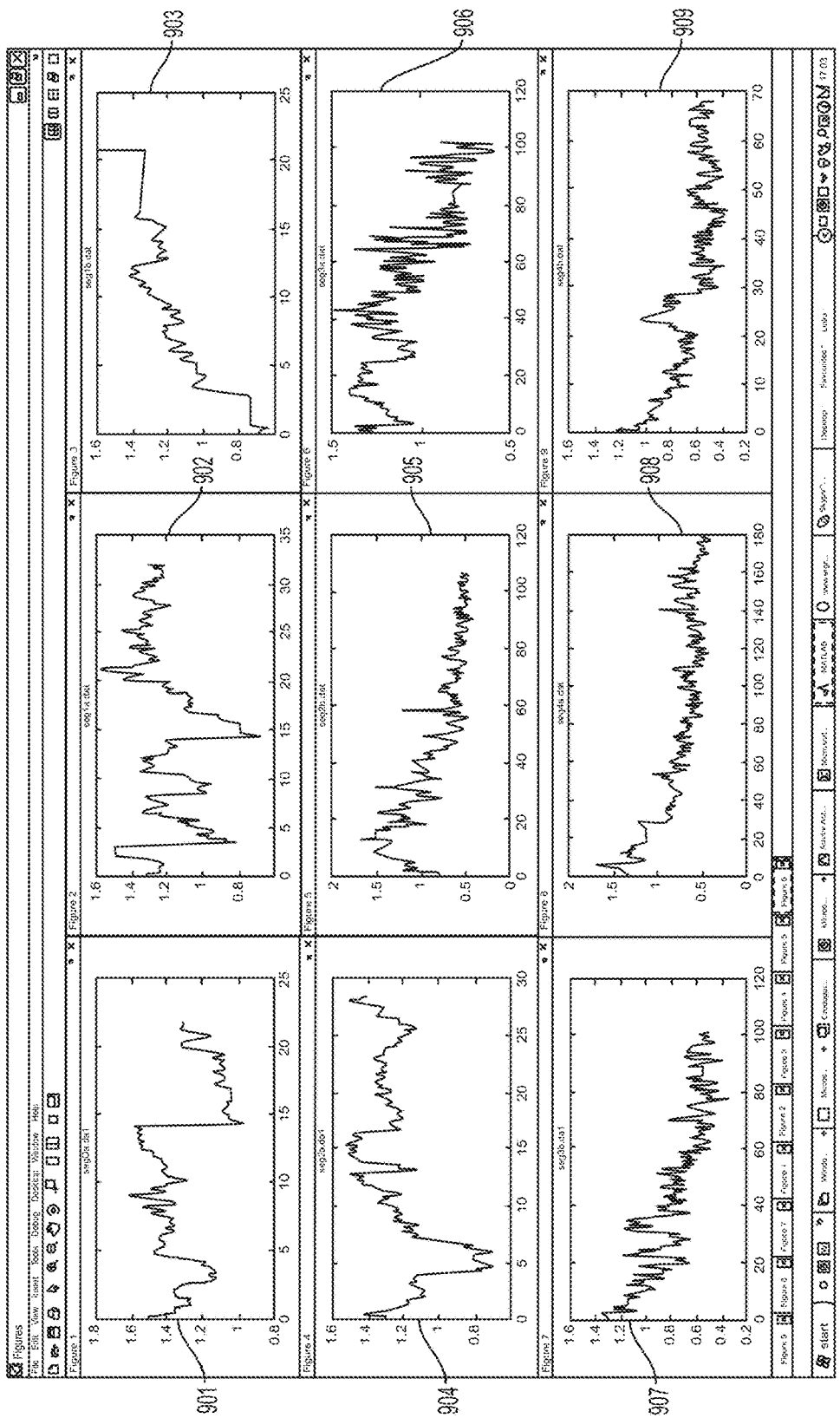
FIG. 4 is a set of nine graphical illustrations of vessel segment radii produced according to an example embodiment of the invention, along the branches of the coronary vessel tree model depicted in FIG. 3C, as a function of distance along each branch.

Reference is now made to FIG. 4, which is a set of nine graphical illustrations 901-909 of vessel segment radii produced according to an example embodiment of the invention, along the branches of the coronary vessel tree model 330 depicted in FIG. 3C, as a function of distance along each branch.

The resistance of a branch to flow is calculated as the sum of the individual resistances of segments along the branch:

$$\mathfrak{R}_{branch} = \int_L \frac{8\mu}{\pi r^4} dl = \frac{8\mu}{\pi} \int_L \frac{dl}{r(l)^4} \quad \text{Equation 5.5}$$

$$\Re_{branch} = \frac{8 \times 0.035_{g/cm \cdot s}}{\pi} \sum \frac{dl_i}{r_i^4} \qquad \text{Equation 5.6}$$

A resistance array corresponding to the example depicted in FIG. 3C is:

Rs=[808 1923 1646 1569 53394 10543 55341 91454 58225], where the resistance to flow is in units of mmHg*s/mL.

The above resistance array is for a vessel with stenosis, as evidenced by a peak of 91454 [mmHg*s/mL] in the resistance array.

A resistance array for a tree model without stenosis is optionally calculated, based on Quantitative Coronary Angiography (QCA) methods for removing stenoses greater than 50% in area.

In some embodiments, a tree model without stenosis is optionally calculated by replacing a stenosed vessel by an inflated vessel, that is, geometric measurements of a stenosed vessel section are replaced by measurements appropriate for an inflated vessel.

In some embodiments geometric data (diameter and/or cross-sectional area) which is used for the inflated vessel is a maximum of the geometric data of the unstenosed vessel at a location just proximal to the stenosed location and at a location just distal to the stenosed location.

In some embodiments geometric data (diameter and/or cross-sectional area) which is used for the inflated vessel is a minimum of the geometric data of the unstenosed vessel at a location just proximal to the stenosed location and at a location just distal to the stenosed location.

In some embodiments geometric data (diameter and/or cross-sectional area) which is used for the inflated vessel is an average of the geometric data of the unstenosed vessel at a location just proximal to the stenosed location and at a location just distal to the stenosed location.

In some embodiments geometric data (diameter and/or cross-sectional area) which is used for the inflated vessel is calculated as a linear function of the geometric data of the unstenosed vessel between a location proximal to the stenosed location and a location distal to the stenosed location, that is, the inflated value is calculated taking into account distances of the stenosed location from the proximal location and from the distal location. A stented, also termed inflated, resistance array for the example depicted in FIG. 4 is:

Rn=[808 1923 1646 1569 53394 10543 55341 80454 51225].

The peak resistance, which was 91454 [mmHg*s/mL], is replaced in the inflated, or stented model, by 80454 [mmHg*s/mL].

Reference is now made to FIG. 5, which depicts a coronary tree model 1010, a combination matrix 1020 depicting tree branch tags, and a combination matrix 1030 depicting tree branch resistances, all produced according to an example embodiment of the invention.

The tree model is an example tree model with nine branches, tagged with branch numbers 0, 1a, 1b, 2a, 2b, 3a, 3b, 4a and 4b.

The combination matrix 1020 includes nine rows 1021-1029, which contain data about nine stream lines, that is, nine paths through which fluid can flow through the tree model. Five of the rows 1025-1029 include data for five full stream lines, in darker text, for five paths which go a full way to outlets of the tree model. Four of the rows 1021-1024 include data for partial streamlines, in lighter text, for four paths which are not fully developed in the tree model, and do not go a full way to outlets of the tree model.

The combination matrix 1030 depicts rows for the same tree model as depicted in the combination matrix 1020, with branch resistances located in matrix cells corresponding to branch tags in the combination matrix 1020.

After calculating a resistance of each branch, stream lines are defined from the tree origin, branch 0 to each outlet. To keep track of the stream lines, branches which constitute each stream line are listed in a combination matrix, as shown for example in FIG. 5.

In some embodiments, defined stream lines are also numbered, as shown in FIG. 6.

Reference is now made to FIG. 6, which depicts a tree model 1100 of a vascular system, with tags 1101-1105 numbering outlets of the tree model 1100, produced according to an example embodiment of the invention, the tags corresponding to stream lines.

A pressure drop along a stream line j is calculated as a sum of pressure drops at each of its component branches (i), according to:

$$dp_j = \Sigma \Re_i Q_i \qquad \text{Equation 5.7}$$

when each branch has a different flow Qi.

Based on a principle of mass conservation at each bifurcation, the flow rate in a mother branch is the sum of flow rates of daughter branches. For example:

$$Q_{1a} = Q_{2a} + Q_{2b} = Q_{4a} + Q_{4b} + Q_{2b} \qquad \text{Equation 5.8}$$

Thus, for example, a pressure drop along a stream line which ends at branch 4a is:

$$\begin{aligned} dp_{4a} &= \Re_0 Q_0 + \Re_{1a} Q_{1a} + \Re_{2a} Q_{2a} + \Re_{4a} Q_{4a} = \\ &\Re_0 (Q_{4a} + Q_{4b} + Q_{2b} + Q_{1a} + Q_{1b}) + \Re_{1a}(Q_{4a} + Q_{4b} + \\ &Q_{2b}) + \Re_{2a}(Q_{4a} + Q_{4b}) + \Re_{4a} Q_{4a} = Q_{4a}(\Re_0 + \\ &\Re_1 + \Re_{2a} + \Re_{4a}) + Q_{4b}(\Re_0 + \Re_{1a} + \Re_{2a}) + \\ &Q_{2b}(\Re_0 + \Re_{1a}) + Q_{3a} \Re_0 + Q_{3b} \Re_0 = Q_4 ER_{4,4} + \\ &Q_5 ER_{4,5} + Q_1 ER_{4,1} + Q_2 ER_{4,2} + Q_3 ER_{4,3} \end{aligned} \qquad \text{Equation 5.9}$$

where Qj is a flow rate along stream line j, and $ER_{4,j}$ is a sum of common resistances of stream line j and stream line 4. A global expression is optionally formulated for the pressure drop along stream line j:

$$dp_j = \Sigma Q_i ER_{i,j} \qquad \text{Equation 5.10}$$

For a tree with k outlet branches, that is, for k full stream lines, a set of k linear equations are optionally used:

$$\begin{bmatrix} ER_{11} & ER_{12} & \ldots & ER_{1k} \\ ER_{21} & ER_{22} & \ldots & ER_{2k} \\ \ldots & & & \\ ER_{k1} & ER_{k2} & \ldots & ER_{kk} \end{bmatrix} \begin{bmatrix} Q_1 \\ Q_2 \\ \ldots \\ Q_k \end{bmatrix} = \begin{bmatrix} dp_1 \\ dp_2 \\ \ldots \\ dp_k \end{bmatrix} \qquad \text{Equation 5.11}$$

$$\overline{\overline{A}} \times \overline{Q} = \overline{DP}$$

where indices 1 . . . k represent stream lines in the tree, and Q1 . . . Qk represent flow rates at corresponding outlet branches. The k×k matrix A consists of elements ER and is calculated from the combination matrix.

For example, for the 5 stream lines tree shown in FIG. 6, the ER matrix is:

$$ER = \begin{bmatrix} (\Re_0 + \Re_{1a} + \Re_{2b}) & (\Re_0) & (\Re_0) & (\Re_0 + \Re_{1a}) & (\Re_0 + \Re_{1a}) \\ (\Re_0) & (\Re_0 + \Re_{1b} + \Re_{3a}) & (\Re_0 + \Re_{1b}) & (\Re_0) & (\Re_0) \\ (\Re_0) & (\Re_0 + \Re_{1b}) & (\Re_0 + \Re_{1b} + \Re_{3b}) & (\Re_0) & (\Re_0) \\ (\Re_0 + \Re_{1a}) & (\Re_0) & (\Re_0) & (\Re_0 + \Re_{1a} + \Re_{2a} + \Re_{4a}) & (\Re_0 + \Re_{1a} + \Re_{2a}) \\ (\Re_0 + \Re_{1a}) & (\Re_0) & (\Re_0) & (\Re_0 + \Re_{1a} + \Re_{2a}) & (\Re_0 + \Re_{1a} + \Re_{2a} + \Re_{4b}) \end{bmatrix}$$

Equation 5.12

$$ER = \begin{bmatrix} 56125 & 808 & 808 & 2731 & 2731 \\ 808 & 12997 & 2454 & 808 & 808 \\ 808 & 2454 & 57795 & 808 & 808 \\ 2731 & 808 & 808 & 95754 & 4300 \\ 2731 & 808 & 808 & 4300 & 55525 \end{bmatrix}$$

Equation 5.13

In some embodiments, fluid pressure measurements are made, for example blood pressure measurements. Based on provided fluid pressure boundary conditions (Pin and Pout_i), a vector $\overline{DP}$ is defined, and Qi is calculated:

$$Q = A^{-1} \times DP$$

Equation 5.14

For example, for a constant pressure drop of 70 mmHg between the origin and all the outlets, the following flow distribution between the outlets is calculated:

Q=[1.4356, 6.6946, 1.2754, 0.7999, 1.4282], where the units of flow are mL/s. The result is an output of the above method, and is depicted in FIG. 7.

Figure 7:
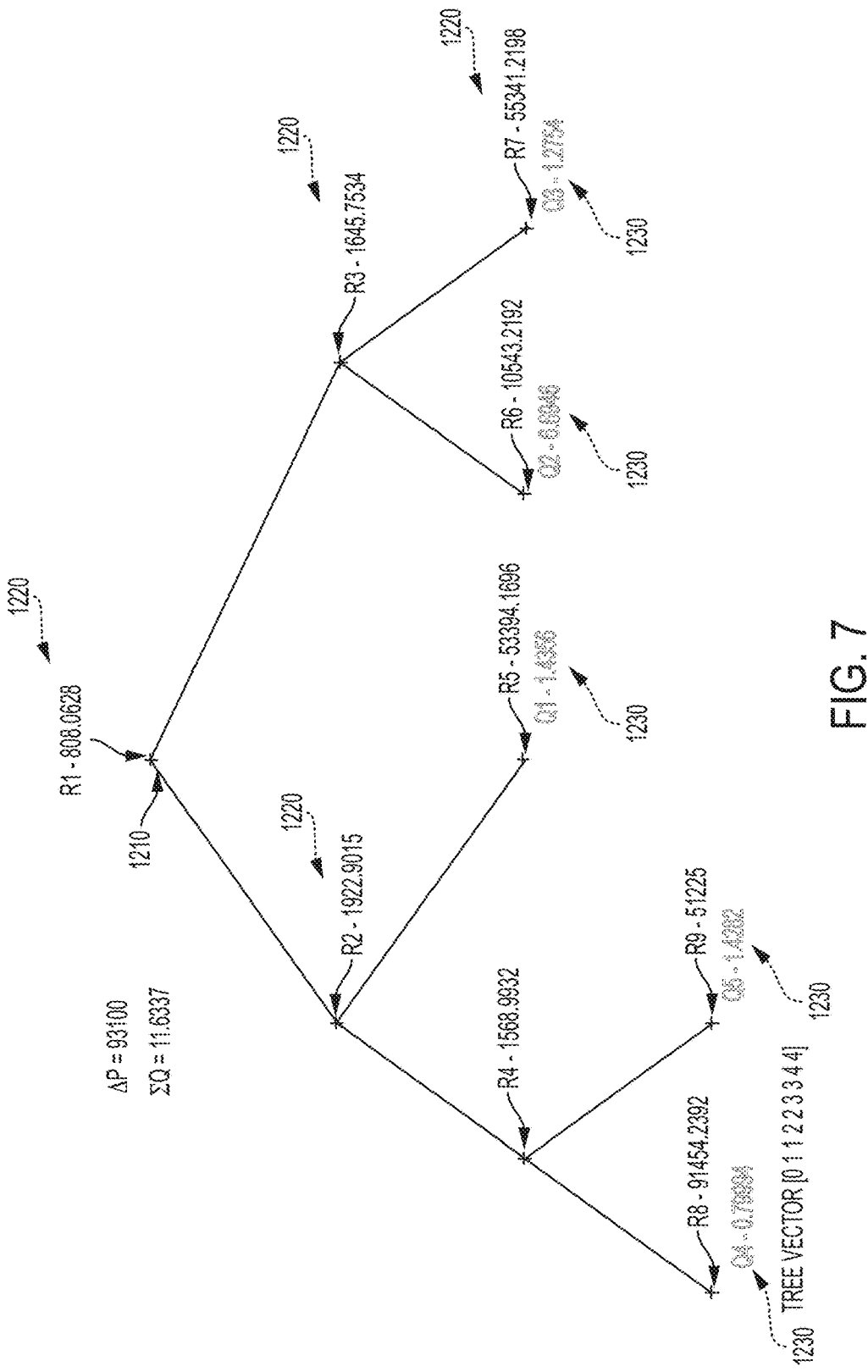
FIG. 7 is a simplified illustration of a vascular tree model produced according to an example embodiment of the invention, including branch resistances Ri at each branch and a calculated flow Qi at each stream line outlet.

Reference is now made to FIG. 7, which is a simplified illustration of a vascular tree model 1210 produced according to an example embodiment of the invention, including branch resistances Ri 1220 [mmHg*s/mL] at each branch and a calculated flow Qi 1230 [mL/s] at each stream line outlet.

In some embodiments, two models of a tree are calculated—a first model with stenoses, optionally as measured for a specific patient, and a second model without stenoses. FFR is calculated for each branch using the formula:

$$FFR = \frac{Q_S}{Q_N}$$

Equation 5.15

For example, for the tree described above, the FFR calculated for each one of the 9 branches is:

FFR=[1.00 1.00 1.00 1.00 1.00 1.00 1.00 0.8846 0.8874]

Some Example Implementation of Calculating an Index

In some embodiments of the invention image processing techniques and numerical calculations are combined for determining a physiological index equivalent to the Fractional Flow Reserve (FFR). The integration of the above-mentioned techniques potentially enables providing a minimally invasive assessment of blood flow during a diagnostic catheterization, and provides an appropriate estimation of the functional significance of coronary lesions.

In some embodiments of the invention, a novel physiological index provides a physiological index which potentially enables evaluating the need for percutaneous coronary intervention, and supports making real-time diagnostic and interventional (treatment) decisions. The minimal-invasive method potentially prevents unnecessary risk to a patient, and may reduce time and cost of angiography, hospitalization and follow-up.

In some embodiments a scientific model, based on patients' data, is provided, which identifies geometrical characteristics of the patient's vascular system, or even a single vessel, and relevant hemodynamic information, equivalent to the present day invasive FFR method.

In addition, the model potentially allows examining a combination of 3D reconstruction of the vessel and a numerical flow analysis for functional significance of a coronary lesion.

Some embodiments of the present invention perform a one-dimensional reconstruction of the coronary artery during coronary angiography and a computational/numerical flow analysis in order to evaluate the arterial pressure and/or flow rate and/or flow resistance along the culprit segment.

Some embodiments of the present invention perform a three-dimensional reconstruction of the coronary artery during coronary angiography and a computational/numerical flow analysis in order to evaluate the arterial pressure and/or flow rate and/or flow resistance along the culprit segment.

In embodiments of the invention in which the vascular function index is calculated based only of the stenotic model, the resistance $R_s$ contributed by a stenosis to the total resistance of the lesion's crown is evaluated. The volume $V_{crown}$ of the crown distal to the stenosis is also calculated. An FFR index can then be calculated as a function which decreases with $R_s$ and $V_{crown}$. A representative example of such a function includes, without limitation, $$FFR = \left(1 + \frac{R_s k V_{crown}^{3/4}}{P_a - P_0}\right)^{-1}$$

Equation 5.15a where $P_a$ is the aortic pressure, $P_0$ is the pre-capillary pressure and k is a scaling law coefficient which can be adapted to the aortic pressure.

Figure 8:
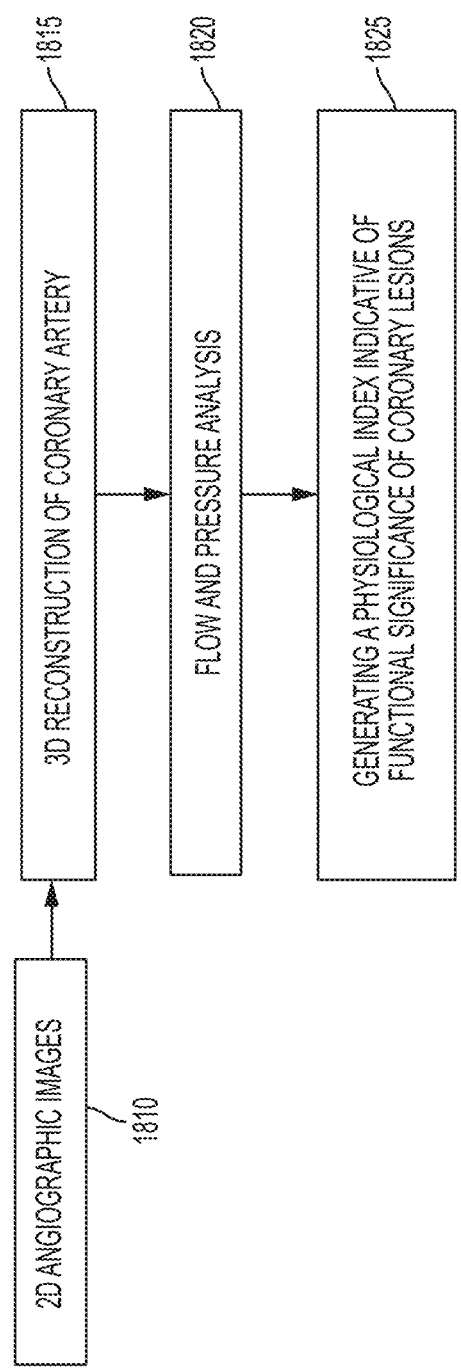
FIG. 8 is a simplified flow chart illustration of an example embodiment of the invention.

Reference is now made to FIG. 8, which is a simplified flow chart illustration of an example embodiment of the invention. This embodiment is particularly useful when a vessel function index, such as FFR is calculated based on two models of the vasculature.

FIG. 8 illustrates some portions of a method according to the example embodiment. The method includes receiving at least two 2D angiographic images of a portion of a coronary artery of a patient (1810) and reconstructing a three-dimensional tree model of a coronary artery system (1815), and if there is a lesion, including the lesion.

A flow analysis of blood flow and optionally arterial pressure along a segment of interest, based on the tree model and optionally on other available hemodynamic measurements, such as aortic pressure and/or amount of injected contrast.

The example embodiment just described potentially provides a minimally-invasive physiological index indicative of functional significance of coronary lesions.

The example method is optionally performed during a coronary angiography procedure, and calculations are optionally performed during the coronary angiography procedure, such that the minimally-invasive physiological index is provided in real-time.

Figure 9:
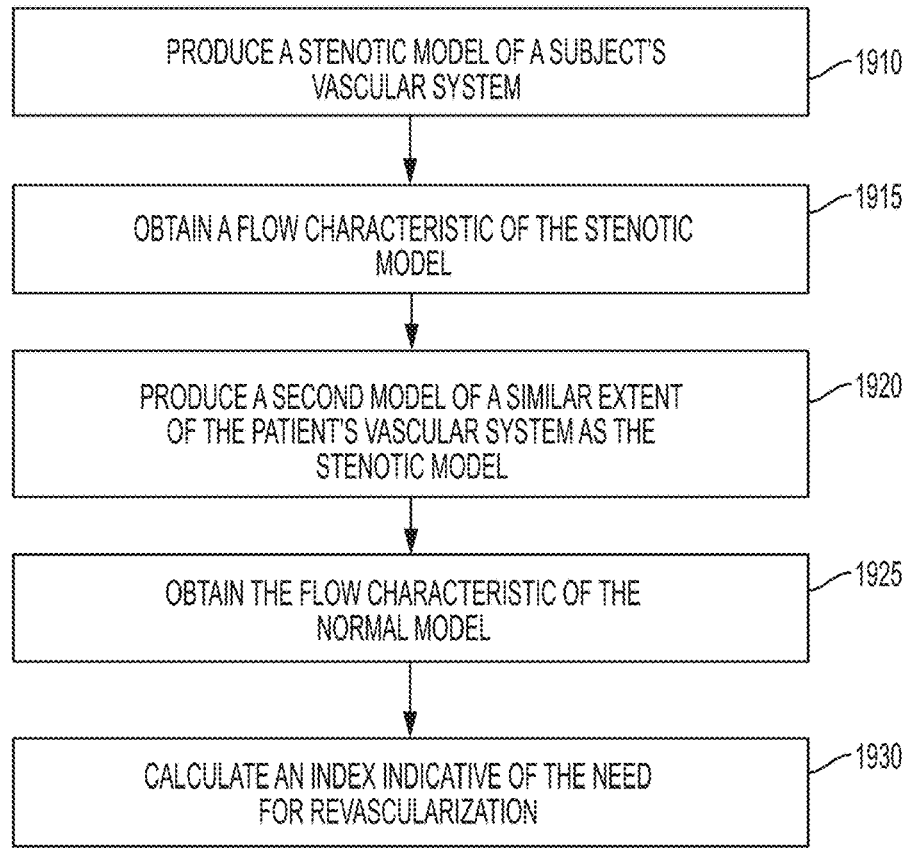
FIG. 9 is a simplified flow chart illustration of another example embodiment of the invention.

Reference is now made to FIG. 9, which is a simplified flow chart illustration of another example embodiment of the invention.

FIG. 9 illustrates a method for vascular assessment which includes:

producing a stenotic model of a subject's vascular system, the stenotic model comprising geometric measurements of the subject's vascular system at one or more locations along a vessel centerline of at least one branch of the subject's vascular system (1910);

obtain a flow characteristic of the stenotic model (1915);

producing a second model of a similar extent of the patient's vascular system as the stenotic model (1920);

obtaining the flow characteristic of the normal model (1925); and calculating an index indicative of the need for revascularization, based on the flow characteristic in the stenotic model and on the flow characteristic in the normal model (1930).

Figure 10:
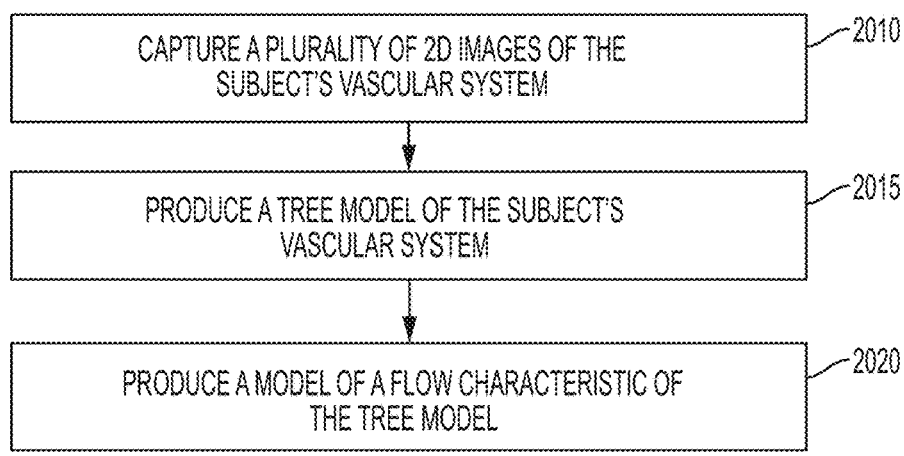
FIG. 10 is a simplified flow chart illustration of yet another example embodiment of the invention.

Reference is now made to FIG. 10, which is a simplified flow chart illustration of yet another example embodiment of the invention.

FIG. 10 illustrates a method for vascular assessment which includes:

capturing a plurality of 2D images of the subject's vascular system (2010);

producing a tree model of the subject's vascular system, the tree model comprising geometric measurements of the subject's vascular system at one or more locations along a vessel centerline of at least one branch of the subject's vascular system, using at least some of the plurality of captured 2D images (2015); and producing a model of flow characteristics of the first tree model (2020).

Extents of the Coronary Tree Model

In some embodiments, the extent of a first, stenosed model is just enough to include a stenosis, a section of vessel proximal to the stenosis, and a section of vessel distal to the stenosis.

In such an embodiment the extent of the first model may be, in some cases a segment of a vessel between bifurcations, including a stenosis in the segment. In some cases, especially when a stenosis is at a bifurcation, the extent may include the bifurcation, and sections of vessels proximal and distal to the stenosed bifurcation.

In some embodiments, an extent by which the first model extends proximal to the stenosis may be as small as 1 or 2 millimeters, up to as much as 20 to 50 millimeters.

In some embodiments, an extent by which the first model extends distal to the stenosis may be as small as 1 or 2 millimeters, up to as much as 20 to 50 millimeters.

In some embodiments, an extent by which the first model extends distal to the stenosis is measured by bifurcations of the vessel. In some embodiments, the first model extends distal to the stenosis by as few as 1 or 2 bifurcations, and in some embodiments by as much as 3, 4, 5, and even more bifurcations. In some embodiments the first model extends distal to the stenosis as far as resolution of the imaging process allows discerning distal portions of the vascular system.

A second model, of the same extent as the first model, is optionally produced, with the stenosis inflated as if the stenosis had been revascularized back to normal diameter.

Producing a Model of Physical Characteristics of a Vascular System

In an example implementation, given a proximal arterial pressure, $P_a$, [mmHg], flow rate through a segment of interest $Q_s$, [mL/s] is optionally derived from a concentration of iodine contrast material, based on an analysis of concentration-distance-time curves, and a geometric description of the segment of interest, including diameter d(l) [cm], and/or volume V(l) [ml] as a function of segment length.

In some embodiments, especially in case of large vessels such as the Left Anterior Descending coronary artery (LAD), blood flow can be measured for obtaining a flow model using a transthoracic echo Doppler, or other modalities such as MRI or SPECT.

For a given segment, a total resistance of the segment ($R_t$, [mmHg*s/mL]) is optionally calculated by: dividing arterial pressure by flow rate:

$$R_t = \frac{P_a}{Q_s} \quad \text{Equation 5.16}$$

where $R_t$ corresponds to total resistance, $P_a$ corresponds to arterial pressure, and $Q_s$ corresponds to flow rate through the vessel segment.

From geometric description of the segment, a local resistance of the stenosis in the segment $R_s$, [mmHg*s/mL] is estimated. Estimation of Rs may be made by any one or more of the following methods: using an empirical lookup table; and/or using a function such as described in the above mentioned Kirkeeide reference; and/or by a cumulative summation of Poiseuille resistances:

$$R_s = \frac{128\mu}{\pi} \int \frac{dl}{d^4} \quad \text{Equation 5.17}$$

where integration is over samples of the segment (dl), d is optionally and arterial diameter of each sample, and µ is 0.035 g/cm·s is optionally blood viscosity.

The segment's downstream resistance is calculated for the segment $R_n$, [mmHg*s/mL] as follows:

$$R_n = R_t - R_s \quad \text{Equation 5.18}$$

A normal flow through the segment without stenosis $Q_n$, [mL/s], is calculated for example as follows:

$$Q_n = \frac{P_a}{R_n} \quad \text{Equation 5.19}$$

where $Q_n$ is an input flow to the segment, $P_a$ is pressure proximal to the segment, and $R_n$ is resistance to flow by vessels distal to the segment.

A Fractional Flow Reserve (FFR) is optionally derived as a ratio between measured flow rate through the stenosed segment and normal flow rate through the segment without stenosis:

$$FFR = \frac{Q_s}{Q_n} \quad \text{Equation 5.20}$$

In some embodiments, an index indicative of the potential effect of revascularization, such as an FFR index, is calculated using the data described below:

proximal arterial pressure Pa, [mmHg] is measured;

a total inlet flow through a vessel origin, such as the coronary origin Qtotal, [mL/s], is derived from a concentration of contrast material (such as iodine), optionally based on the analysis of concentration-distance-time curves. In some embodiments, especially for large vessels such as the Left Anterior Descending (LAD) coronary artery, flow is optionally recorded using a transthoracic echo Doppler and/or other modalities such as MRI and SPECT;

a subject's specific anatomy, including one or more of the following:

a geometric description of arterial diameters along vessel tree segments, for example up to 3-4 generations as a function of segment length d(l) [cm];

a geometric description of arterial lengths along the vessel tree segments (Li [cm]). for example up to 1-2 generations downstream of the segment of interest, and an accumulative crown length ($L_{crown}$ [cm]) downstream to the segment of interest: $L_{crown} = \Sigma L_i$;

a geometric description of arterial volumes along the vessel tree segments Vi [ml], for example up to 1-2 generations downstream of the segment of interest, and the accumulative crown volume ($V_{crown}$ [ml]) downstream to the segment of interest: $V_{crown} = \Sigma V_i$;

a myocardial mass (LV mass) distribution for the arterial segment of interest M [ml]. in some embodiments LV mass is optionally calculated using, for example, a transthoracic echo Doppler;

and a reference parameter K or function F which correlates anatomic parameters such as described above with normal flow through the segment (without stenosis) Qn, [mL/s], for example:

$$Q_n = K*M \text{ or } Q_n = F(M) \qquad \text{Equation 5.21}$$

Using the above data, the index indicative of the potential effect of revascularization, such as the FFR index, is optionally calculated by performing the following calculations for each vessel segment under consideration:

from the geometric parameter of the tree, such as length, volume, mass and/or diameter, a normal flow Qn in the segment is obtained;

from arterial pressure a resistance distal to the segment (Rn, [mmHg*s/mL]) is calculated, for example as follows:

$$R_n = \frac{P_a}{Q_n};$$

from geometry a local resistance of the stenosis in the segment Rs, [mmHg*s/mL] is estimated, for example using one of the following methods:

a lookup table;

an empirical function such as described in the above mentioned Kirkeeide reference; and/or a cumulative summation of Poiseuille resistance $$R_s = \frac{128\mu}{\pi} \int \frac{dl}{d^4}$$

where the integration is over samples of the segment (dl), d is an arterial diameter of each sample, and μ is 0.035 g/cm·s is optionally blood viscosity;

the total resistance for the segment RI [mmHg*s/mL] is optionally calculated as: $R_t = R_n + R_s$ the flow through the stenosis segment Qs [mL/s] is optionally calculated as:

$$Q_s = \frac{P_a}{R_t};$$

and the index, such as the fractional flow reserve (FFR), for the segment is optionally calculated as:

$$FFR = \frac{Q_s}{Q_n}.$$

It is noted that a sanity check for the above calculation can optionally be made by checking if the accumulated flow in the tree agrees with the measured total flow as follows: $Q_{total} = \Sigma Q_i$.

In some embodiments, the extent of the first model is such that it includes a stenosis, and extends distally as far as resolution of the imaging modality which produced the vessel model allows, and/or several bifurcations, for example 3 or 4 bifurcations distally to the stenosis.

In an example implementation, a total inlet flow through a coronary origin is optionally derived from a concentration of contrast material and optionally a subject's specific anatomy.

In some embodiments, data regarding the anatomy optionally includes a geometric description of arterial diameters along vessel segments up to 3-4 bifurcations distally to a stenosis, a geometric description of arterial lengths along vessel tree segments, a geometric description of arterial volumes along the tree segments, and/or a myocardial mass (LV mass) distribution for the arterial segment of interest.

In some embodiments, data regarding the anatomy optionally includes a geometric description of arterial diameters along vessel segments as far as the imaging modality allows distally to a stenosis, a geometric description of arterial lengths along vessel tree segments, a geometric description of arterial volumes along the tree segments, and/or a myocardial mass (LV mass) distribution for the arterial segment of interest.

In some embodiments, LV mass is optionally calculated by using a transthoracic echo Doppler.

In some embodiments, a reference scaling parameter or function which correlates anatomic parameters with normal flow through a segment without stenosis is used.

In some embodiments, the extent of a first model includes a stenosed vessel, and a second model includes a similar extent of the vascular system, with a healthy vessel similar to the stenosed vessel.

An FFR index is optionally calculated from a ratio between the measured flow rate in a stenosed vessel, and a flow rate in a neighboring healthy vessel. In some embodiments, the index is adjusted by a proportion between a total length of vessels in the crowns of the stenosed vessel and the healthy vessel. A crown of a vessel is hereby defined as a sub-tree branching off the vessel. The total length of a crown is optionally derived from a 3D reconstruction of the coronary tree.

Figure 11:
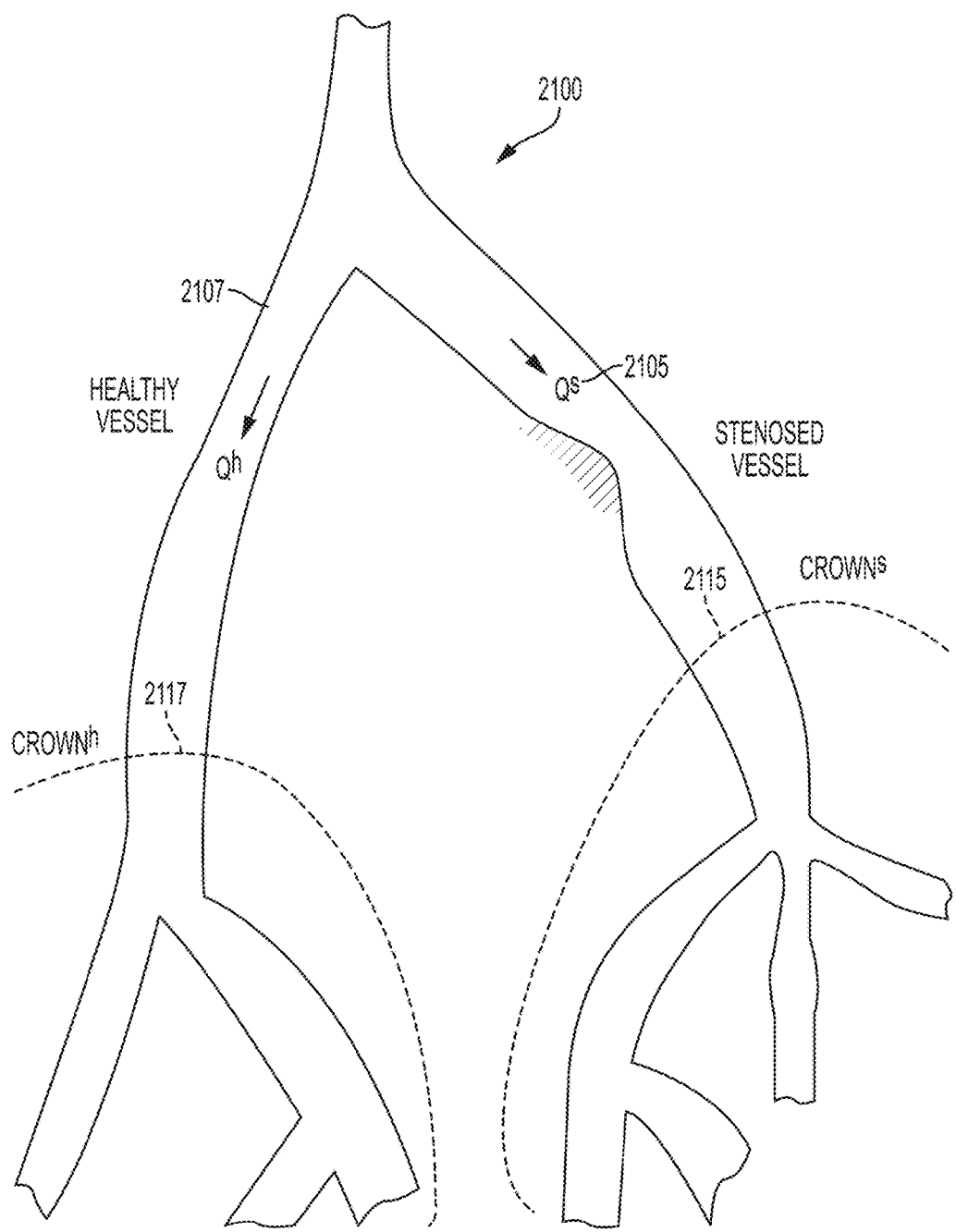
FIG. 11 is a simplified drawing of vasculature which includes a stenosed vessel and a non-stenosed vessel.

Reference is now made to FIG. 11, which is a simplified drawing 2100 of vasculature which includes a stenosed vessel 2105 and a non-stenosed vessel 2107.

FIG. 11 depicts two vessels which are candidates for basing a flow characteristic comparison of the stenosed vessel 2105 and the non-stenosed vessel 2107. FIG. 11 also depicts the stenosed vessel crown 2115 and the non-stenosed vessel crown 2117.

It is noted that the two vessels in FIG. 11 seem to be especially good candidates for the comparison, since both seem to have similar diameters, and both seem to have similar crowns.

According to scaling laws, a linear relationship exists between a normal flow rate Q in an artery, and a total length of vessels in its crown. This relationship holds for both the neighboring healthy vessel, and the stenosed vessel. For a healthy vessel:

$$Q_N^h = k*L^h \qquad \text{Equation 6.1}$$

where $Q_N^h$ is a flow rate of a healthy vessel, k is a correction factor, and $L^h$ is a total length of crown vasculature of the healthy vessel.

For a stenosed vessel, similarly:

$$Q_N^s = k*L^s \qquad \text{Equation 6.2}$$

where $Q_N^s$ is a flow rate of a stenosed vessel, k is a correction factor, and $L^s$ is a total length of crown vasculature of the stenosed vessel.

FFR is defined as a ratio between a flow rate in a stenosed artery during hyperemia, and the flow rate in the same artery in the absence of the stenosis (normal flow rate), as described by Equation 6.3 below. The above relationship yields a result for the FFR, calculated as a ratio between the measured flow rates in both vessels divided by the ratio between their respective total crown lengths.

It is noted that scaling laws also state the relationship between the normal flow rate and the total crown volume. In some embodiments, the index or FFR is optionally calculated from the above-mentioned ratio between the measured flow rates in the sick and healthy arteries, divided by a ratio between respective total crown volumes of a stenosed vessel and a normal vessel respectively, to the power of ¾.

$$FFR \equiv \frac{Q_S^s}{Q_N^s} = \frac{Q_S^s}{k*L^s} = \frac{Q_S^s}{\frac{Q_N^h}{L^h}*L^s} = \left(\frac{Q_S^s}{Q_N^h}\right)*\frac{L^h}{L^s} \qquad \text{Equation 6.3}$$

Where $Q_N^s$ is an existing flow in a stenosed vessel, measured by any method described herein; $Q_N^h$ is an existing flow in a healthy vessel, measured by any method described herein; $L^s$ is a total crown length of the stenosed vessel; and $L^h$ is a total crown length of the healthy vessel.

The scaling laws also state a relationship between a normal flow rate and a total crown volume:

$$Q_N^h = k_v * V_h^{3/4} \qquad \text{Equation 6.4}$$

where $Q_N^h$ is a flow rate of a healthy vessel, $k_v$ is a correction factor, and $V_h$ is a total volume of crown vasculature of the healthy vessel.

For a stenosed vessel, similarly:

$$Q_N^s = k_v * V_s^{3/4} \qquad \text{Equation 6.5}$$

where $Q_N^s$ is a flow rate of a stenosed vessel, $k_v$ is a correction factor, and $V_h$ is a total volume of crown vasculature of the stenosed vessel.

An FFR is optionally calculated from the above-mentioned ratio between the measured flow rates in the sick and healthy vessels, divided by the ratio between the respective total crown volumes, raised to the power of ¾:

$$FFR = \left(\frac{Q_S^s}{Q_N^h}\right) * \left(\frac{V_h}{V_s}\right)^{3/4} \qquad \text{Equation 6.6}$$

where Vh and Vs are measured, by way of a non-limiting example, by using a 3D model of the vasculature.

An Example Hardware Implementation

Figure 12A:
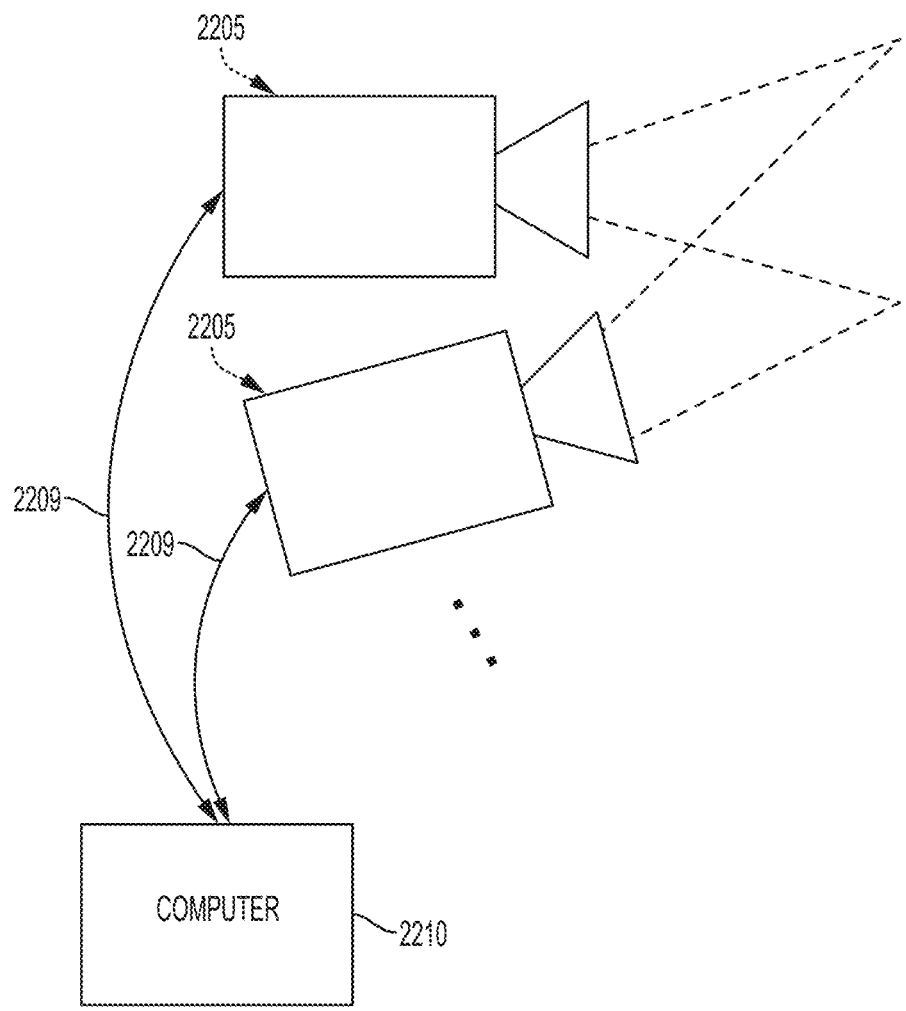
FIG. 12A is a simplified illustration of a hardware implementation of a system for vascular assessment constructed according to an example embodiment of the invention.

Reference is now made to FIG. 12A, which is a simplified illustration of a hardware implementation of a system for vascular assessment constructed according to an example embodiment of the invention.

The example system of FIG. 12A includes:

Two or more imaging devices 2205 for capturing a plurality of 2D images of the patient's vascular system; a computer 2210 functionally connected 2209 to the two or more imaging devices 2205.

The computer 2210 is optionally configured to: accept data from the plurality of imaging devices 2205; produce a tree model of the patient's vascular system, wherein the tree model comprises geometric measurements of the patient's vascular system at one or more locations along a vessel centerline of at least one branch of the patient's vascular system, using at least some of the plurality of captured 2D images; and produce a model of flow characteristics of the tree model.

In some embodiments a synchronization unit (not shown) is used to provide the imaging devices 2205 with a synchronization signal for synchronizing the capturing of 2D images of the patient's vascular system.

Figure 12B:
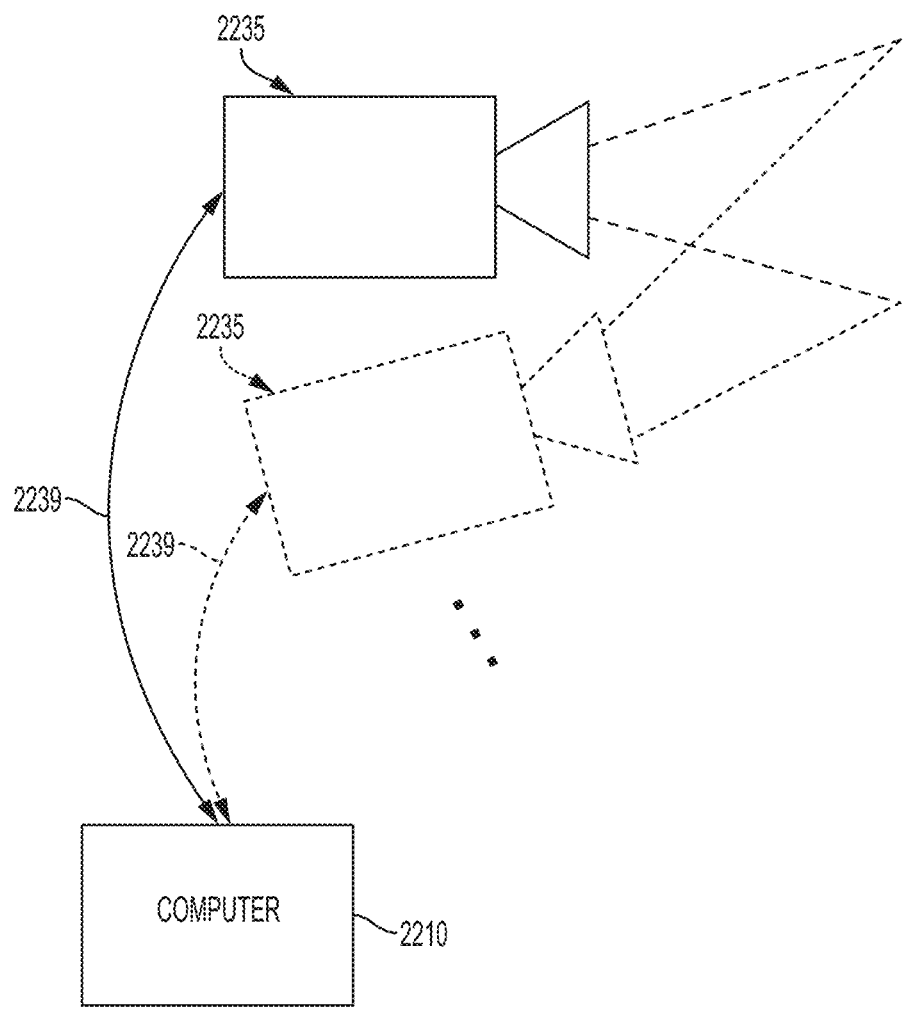
FIG. 12B is a simplified illustration of another hardware implementation of a system for vascular assessment constructed according to an example embodiment of the invention.

Reference is now made to FIG. 12B, which is a simplified illustration of another hardware implementation of a system for vascular assessment constructed according to an example embodiment of the invention.

The example system of FIG. 12B includes:

One imaging device 2235 for capturing a plurality of 2D images of the patient's vascular system and a computer 2210 functionally connected 2239 to the imaging device 2235.

In the example embodiment of FIG. 12B, the imaging device 2235 is configured to obtaining the 2D images from two or more directions with respect to the subject. The direction and location of the imaging device 2235 with respect to the subject, and/or with respect to a fixed frame of reference, are optionally recorded, optionally to aid in producing a vessel tree model, whether 1 dimensional (1D) or three dimensional (3D), from 2D Images taken by the imaging device 2235.

The computer 2210 is optionally configured to: accept data from the plurality of imaging device 2235; produce a tree model of the patient's vascular system, wherein the tree model comprises geometric measurements of the patient's vascular system at one or more locations along a vessel centerline of at least one branch of the patient's vascular system, using at least some of the plurality of captured 2D images; and produce a model of flow characteristics of the tree model.

In some embodiments a synchronization unit (not shown) is used to provide the imaging device 2235 with a synchronization signal for synchronizing the capturing of 2D images of the patient's vascular system, optionally at a same phase during the cardiac cycle.

In some embodiments the computer 2210 accepts a subject's ECG signal (not shown), and selects 2D images from the imaging device 2235 according to the ECG signal, for example in order to select 2D images at a same cardiac phase.

In some embodiments, the system of FIG. 12A or 12B includes an image registration unit which detects corresponding image features in the 2D images; calculates image correction parameters based on the corresponding image features; and registers the 2D images so the image features correspond geometrically.

In some embodiments the image features are optionally selected as an origin of the tree model; and/or a location of minimal radius in a stenosed vessel; and/or a bifurcation of a vessel.

Potential Benefits of Embodiments of the Invention

Example embodiments of the invention can be minimally invasive, that is, they can refrain from guidewire interrogation of the coronary artery, and therefore minimize danger to a patient, compared to an invasive FFR catheter procedure.

It is noted that an example embodiment of the invention enables measuring a reliable index during catheterization, providing a cost-effective way to potentially eliminate a need for processing angiographic data after the catheterization procedure, and/or for additional equipment during the catheterization procedure, such as a guidewire, and/or for materials involved in a catheterization procedure, such as adenosine. It is noted that another potential saving includes a saving in hospitalization costs following better treatment decisions.

An example embodiment of the invention optionally enables trying out various post-inflation vessel cross sections in various post-inflation models of the vascular system, and selecting a suitable stent for a subject based on desired flow characteristics of the post-inflation model.

An example embodiment of the invention optionally automatically identifies geometrical characteristics of a vessel, defines an outer contour of the vessel, and optionally provides relevant hemodynamic information associated with the vessel, corresponding to the present-day invasive FFR method.

An embodiment of the invention optionally generates an index indicative of a need for coronary revascularization. The minimally invasive embodiment of the invention potentially prevents unnecessary risk to patients, potentially reduces total time and cost of an angiography, hospitalization and follow-up.

A system constructed according to an example embodiment of the invention potentially enables shortening the diagnostic angiography procedure. Unnecessary coronary interventions during angiography and/or in the future are also potentially prevented. Also, a method according to an example embodiment of the invention optionally enables assessment of vascular problems in other arterial territories, such as carotid arteries, renal arteries, and diseased vessels of the limbs.

It is noted that resolution of angiographic images is typically higher than resolution typically obtained by 3D techniques such a CT. A model constructed from the higher resolution angiographic images can be inherently higher resolution, and provide greater geometric accuracy, and/or use of geometric properties of smaller vessels than CT images, and/or calculations using branching vessels distal to a stenosis for more generations, or bifurcations, downstream from the stenosis than CT images.

A short list of potential non-invasive FFR benefits includes: a non-invasive method which does not endanger the patient; a computational method without additional time or invasive equipment; a prognostic benefit in 'borderline' lesions and in multi-vessel disease; provides a reliable index to assess the need for coronary revascularization; a method to assess and/or optimize revascularization procedures; a strategy which saves cost of catheterization, hospitalization and follow-up; preventing unnecessary coronary interventions following angiography; and a 'one-stop shop' comprehensive lesion assessment.

Another benefit of the present embodiments is the ability to produce a tree model within a short period of time. This allows calculating of indices, particularly but not necessarily, indices that are indicative of vascular function (e.g., FFR) also within a short period of time (e.g., within less than 60 minutes or less than 50 minutes or less than 40 minutes or less than 30 minutes or less than 20 minutes from the time at which the 2D images are received by the computer). Preferably, the index is calculated while the subject is still immobilized on the treatment surface for the porpoise of catheterization. Such fast calculation of index is advantageous since it allows the physician to get the assessment for a lesion being diagnosed during the catheterization procedure, and thus enable quick decision regarding the proper treatment for that lesion. The physician can determine the necessity of treatment while being in the catheterization room, and does not have to wait for an offline analysis.

Additional advantageous of fast calculation of index include, reduced risk to the patient, ability to calculate the index without the need of drugs or invasive equipment, shortening of the duration of coronary diagnostic procedure, established prognostic benefit in borderline lesions, reduced costs, reduced number of unnecessary coronary interventions and reduced amount of subsequent procedures.

The In this "game" of assessing the hemodynamic severity of each lesion, a non-real-time solution is not a considered option. The physician needs to know whether to treat the lesion in the cath lab or not, and can't afford to wait for an offline analysis. CT-based solutions are also part of a different "game", since the utilization of cardiac CT scans is low compared to PCI procedures, and the resolution, both temporal and spatial, is much lower compared to angiograms.

Another point to stress, is that the on-line image-based FFR evaluation, unlike the invasive evaluation, will allow to assess any borderline lesion, and won't be necessarily limited to the percentage of lesions evaluated nowadays, since the risk to the patient, and the cost will be a lot lower.

It is expected that during the life of a patent maturing from this application many relevant methods and systems for imaging a vascular system will be developed and the scope of terms describing imaging are intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention is claimed as follows:

1. A vascular assessment apparatus comprising:
a processor communicatively coupled to a medical imaging device; and
a memory storing non-transitory computer-readable instructions, which when executed, cause the processor to:
receive medical images of a coronary vessel tree of a subject from the medical imaging device;
analyze the medical images to identify vessel segments within the coronary vessel tree including vessel segments that are located before or after bifurcations and/or trifurcations of the coronary vessel tree;
for each identified vessel segment:
analyze portions of the segment to determine at least one of a radius, diameter, or cross-sectional area of the vessel segment at the analyzed portions,
determine resistances for the analyzed portions of the vessel segment based on the least one of the radius, diameter, or the cross-sectional area at the analyzed portions, and
combine the determined resistances for the analyzed portions of the vessel segment to determine a total resistance of the identified vessel segment;
determine relative flow rates for each vessel segment based on mass conservation;
determine a relative pressure drop at each identified vessel segment based on total resistances and relative flow rates for the identified vessel segment and upstream vessel segments;
determine flow rates for each vessel segment based on the relative pressure drops at the respective vessel segment;
calculate an index indicative of vascular function, based, at least in part, on the determined flow rates; and
cause the index indicative of vascular function to be displayed.

2. The vascular assessment apparatus of claim 1, further comprising stored non-transitory computer-readable instructions, which when executed, cause the processor to:
determine a pressure drop at each identified vessel segment by multiplying the relative pressure drop for the identified vessel segment by a blood pressure of the subject; and
determine the flow rate for each vessel segment based on the pressure drop at the respective vessel segment.

3. The vascular assessment apparatus of claim 2, wherein the blood pressure includes an aortic pressure.

4. The vascular assessment apparatus of claim 1, further comprising stored non-transitory computer-readable instructions, which when executed, cause the processor to determine the total resistance (R) for each of the identified vessel segments based on equation (1), $$R = \frac{8\mu}{\pi} \int_O^L \frac{dl}{r(l)^4} \qquad \text{(equation 1)}$$

where μ is blood viscosity, r(l) is the radius of the vessel segment at the analyzed portion, and L is a length of the vessel segment.

5. The vascular assessment apparatus of claim 1, wherein the analyzed portions of the vessel segments are spaced apart by a distance that is between 0.1 millimeters ("mm") and 5 mm.

6. The vascular assessment apparatus of claim 1, wherein the total resistance for each of the identified vessel segments is in units of mmHg*s/mL.

7. The vascular assessment apparatus of claim 1, further comprising stored non-transitory computer-readable instructions, which when executed, cause the processor to determine the relative flow rates for each vessel segment by, for each bifurcation or trifurcation of the coronary vessel tree, equating a relative flow rate of an upstream vessel segment connected to the bifurcation or trifurcation to a sum of relative flow rates of vessel segments that exit the bifurcation or trifurcation.

8. The vascular assessment apparatus of claim 1, further comprising stored non-transitory computer-readable instructions, which when executed, cause the processor to:
   determine which of the vessel segments include outlets from the coronary vessel tree;
   designate a vascular stream for each flow path from an entry vessel segment through downstream vessel segments ending at one of the vessel segments that include an outlet; and
   create an M×N resistance matrix where M and N each correspond to a number of vascular streams, and values of matrix entries (i,j) of the M×N resistance matrix correspond to sums of common resistances among i-th and j-th vascular streams.

9. The vascular assessment apparatus of claim 8, further comprising stored non-transitory computer-readable instructions, which when executed, cause the processor to determine the relative pressure drop at each of the identified vessel segments by determining a pressure drop along each of the vascular streams ($dp_j$) according to equation 2

$$dp_j = \Sigma Q_j * ER_{ij} \quad \text{(equation 2)}$$

where j is the stream number from the M×N resistance matrix, $Q_j$ is a relative flow rate along vascular stream j, and ERi,j is the sum of common resistances between vascular stream i and vascular stream j from the M×N resistance matrix.

10. The vascular assessment apparatus of claim 1, further comprising stored non-transitory computer-readable instructions, which when executed, cause the processor to receive the blood pressure of the subject as a blood pressure measurement of the subject.

11. The vascular assessment apparatus of claim 1, further comprising stored non-transitory computer-readable instructions, which when executed, cause the processor to:
   analyze the total resistances of the vessel segments to identify a peak resistance corresponding to a stenosis;
   preform a virtual revascularization of the vessel segment to remove the stenosis;
   determine at least one of a new radius, new diameter, or new cross-sectional area of at least some of the portions of the vessel segment with the stenosis virtually removed;
   determine a new total resistance of the vessel segment with the stenosis virtually removed;
   re-calculate the relative flow rates, the relative pressure drops, and the flow rates for the vessel segments based on the new total resistance of the vessel segment with the stenosis virtually removed;
   calculate a second index indicative of vascular function, based, at least in part, on the re-calculated flow rates; and
   cause the second index of indicative of vascular function to be displayed.

12. The vascular assessment apparatus of claim 11, further comprising stored non-transitory computer-readable instructions, which when executed, cause the processor to:
   create a ratio between the index and the second index; and
   cause the ratio to be displayed indicative of a severity of the stenosis.

13. The vascular assessment apparatus of claim 12, wherein the index of vascular function and the second index of vascular function include flow rates for each of the vascular streams, and a ratio is created for each vascular stream.

14. The vascular assessment apparatus of claim 12, further comprising stored non-transitory computer-readable instructions, which when executed, cause the processor to:
   compare the ratio to a predetermined value; and
   display an indication for stent placement based on the comparison.

15. The vascular assessment apparatus of claim 12, wherein the predetermined value is between 0.75 and 0.8.

16. The vascular assessment apparatus of claim 11, wherein the ratio includes at least one Fractional Flow Ratio ("FFR").

17. The vascular assessment apparatus of claim 11, further comprising stored non-transitory computer-readable instructions, which when executed, cause the processor to perform the virtual revascularization of the vessel segment to remove the stenosis by determining the at least one of a new radius, new diameter, or new cross-sectional area of at least some of the portions of the vessel segment based on at least one of radii or cross-sectional areas of adjacent portions of the vessel segment.

18. The vascular assessment apparatus of claim 1, further comprising stored non-transitory computer-readable instructions, which when executed, cause the processor to:
   create a model illustrative of locations and relationships of the vessel segments, the vascular streams, and the bifurcations and/or trifurcations of the coronary vessel tree;
   color-code the model based on the index of indicative of vascular function; and
   cause the model to be displayed.

19. The vascular assessment apparatus of claim 1, wherein the medical imaging device is a computerized tomography (CT) machine and the medical images include CT images.

20. A vascular assessment apparatus storing non-transitory computer-readable instructions, which when executed, cause the apparatus to:
   receive a stenotic model having measurements of a coronary vessel tree of a subject, the stenotic model created from medical images of the coronary vessel tree of the subject;
   identify vessel segments within the stenotic model;
   for each identified vessel segment:
      analyze portions of the segment to determine at least one of a radius, diameter, or cross-sectional area of the vessel segment at the analyzed portions,
      determine resistances for the analyzed portions of the vessel segment based on the least one of the radius, diameter, or cross-sectional area at the analyzed portions, and
      combine the determined resistances for the analyzed portions of the vessel segment to determine a total resistance of the identified vessel segment,
   determine relative flow rates for the vessel segments;
   determine which of the vessel segments include outlets from the coronary vessel tree;
   designate a vascular stream for each flow path from an entry vessel segment through downstream vessel segments ending at one of the vessel segments that include an outlet;
   determine a relative pressure drop at each vascular stream based on total resistances and relative flow rates for the vascular stream and other vascular streams that share common vessel segments;
   determine flow rates for the vascular streams based on the relative pressure drops at the vascular streams;

calculate an index indicative of vascular function for the vascular streams, based, at least in part, on the determined flow rates; and cause the index indicative of vascular function to be displayed.

21. The vascular assessment apparatus of claim 20, wherein the stenotic model includes at least one of a three-dimensional model or a two-dimensional model of the coronary vessel tree.

22. The vascular assessment apparatus of claim 20, wherein the stenotic model is created from at least one of a set of computerized tomography (CT) images or angiographic images.

23. The vascular assessment apparatus of claim 20, further comprising stored non-transitory computer-readable instructions, which when executed, cause the apparatus to:

determine a curvature for at least one of the vessel segments;

determine a curvature resistance based on the determined curvature; and add the determined curvature resistance to the total resistance for the vessel segment.

24. The vascular assessment apparatus of claim 20, further comprising stored non-transitory computer-readable instructions, which when executed, cause the apparatus to:

determine a pressure drop at each identified vessel segment by multiplying the relative pressure drop for the identified vessel segment by a blood pressure of the subject; and determine the flow rates for each vessel segment based on the pressure drops at the respective vessel segment.

* * * * *